(12) United States Patent
Thatcher et al.

(10) Patent No.: US 6,218,112 B1
(45) Date of Patent: Apr. 17, 2001

(54) OPTIMIZATION OF GENE DELIVERY AND GENE DELIVERY SYSTEM

(75) Inventors: David R. Thatcher, Macclesfield; Paula E. Wilks, Alsager Stoke on Trent, both of (GB)

(73) Assignee: Cobra Therapeutics Limited (GB)

( * ) Notice: Subject to any disclaimer, the term of this patent is extended or adjusted under 35 U.S.C. 154(b) by 0 days.

(21) Appl. No.: 08/995,172

(22) Filed: Dec. 22, 1997

Related U.S. Application Data

(60) Provisional application No. 60/033,908, filed on Dec. 23, 1996.

(51) Int. Cl.[7] .................................................. C12Q 1/68
(52) U.S. Cl. ............................. 435/6; 435/456; 435/458
(58) Field of Search .......................... 435/172.3, 6, 456, 435/458

*Primary Examiner*—James Ketter
(74) *Attorney, Agent, or Firm*—Woodcock Washburn Krutz Mackiewicz & Norris LLP

(57) ABSTRACT

Methods of screening for peptides useful in a gene delivery system to provide optimal transfection of cells based on kinetic parameters of the peptide-nucleic acid bimolecular interaction are described.

20 Claims, 9 Drawing Sheets

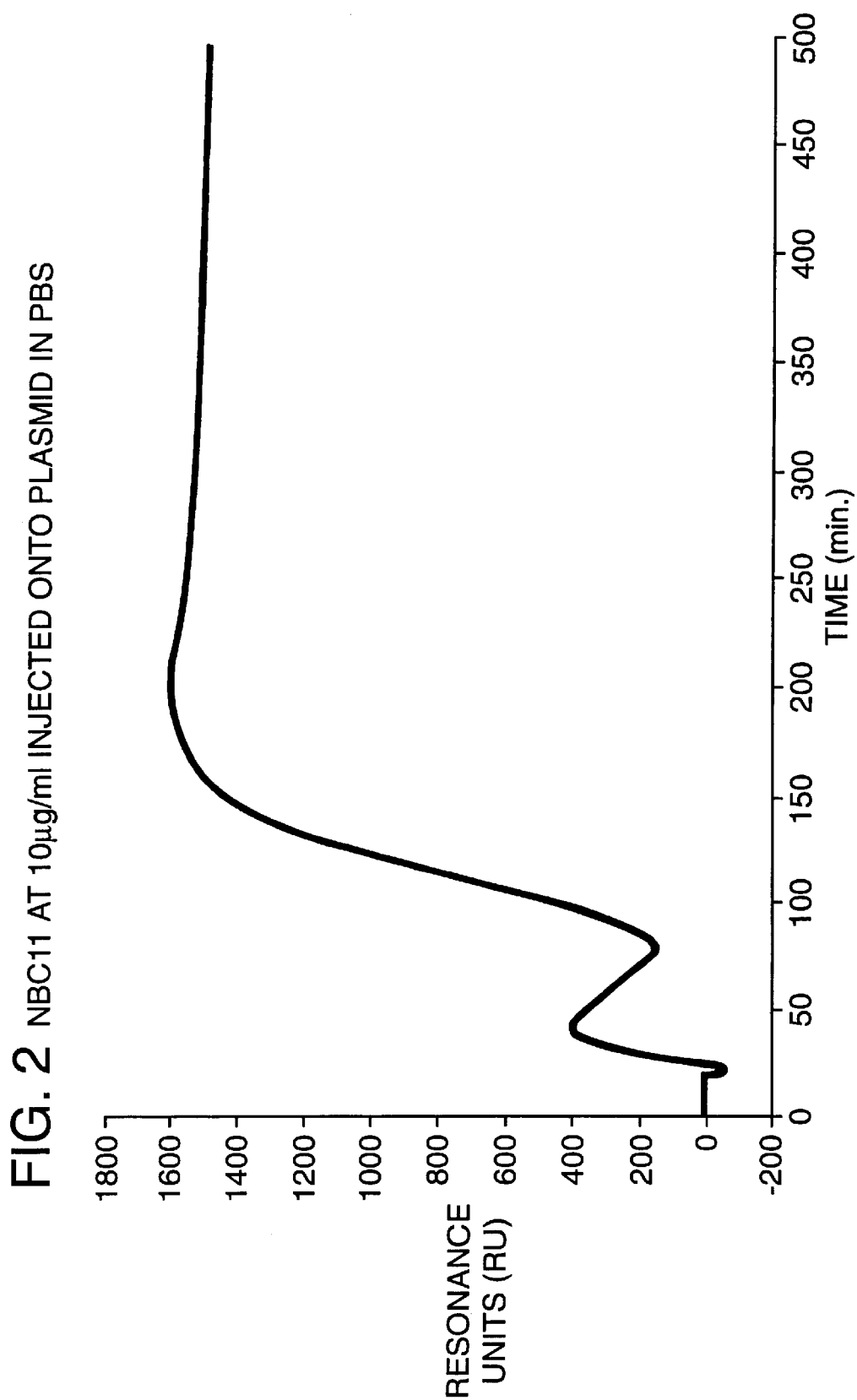

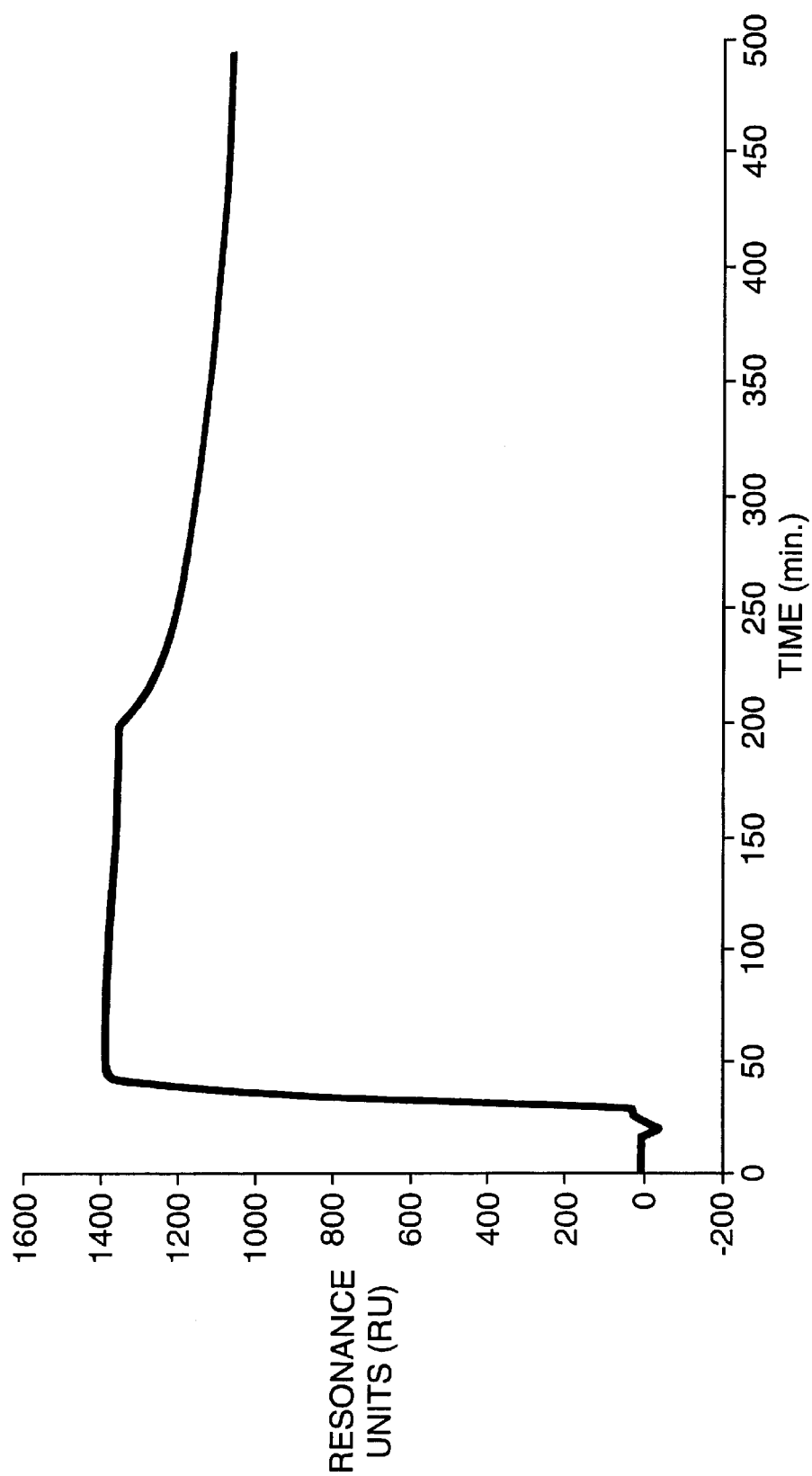
FIG. 3 Lip9 AT 20μg/ml INJECTED INTO PLASMID IN PBS

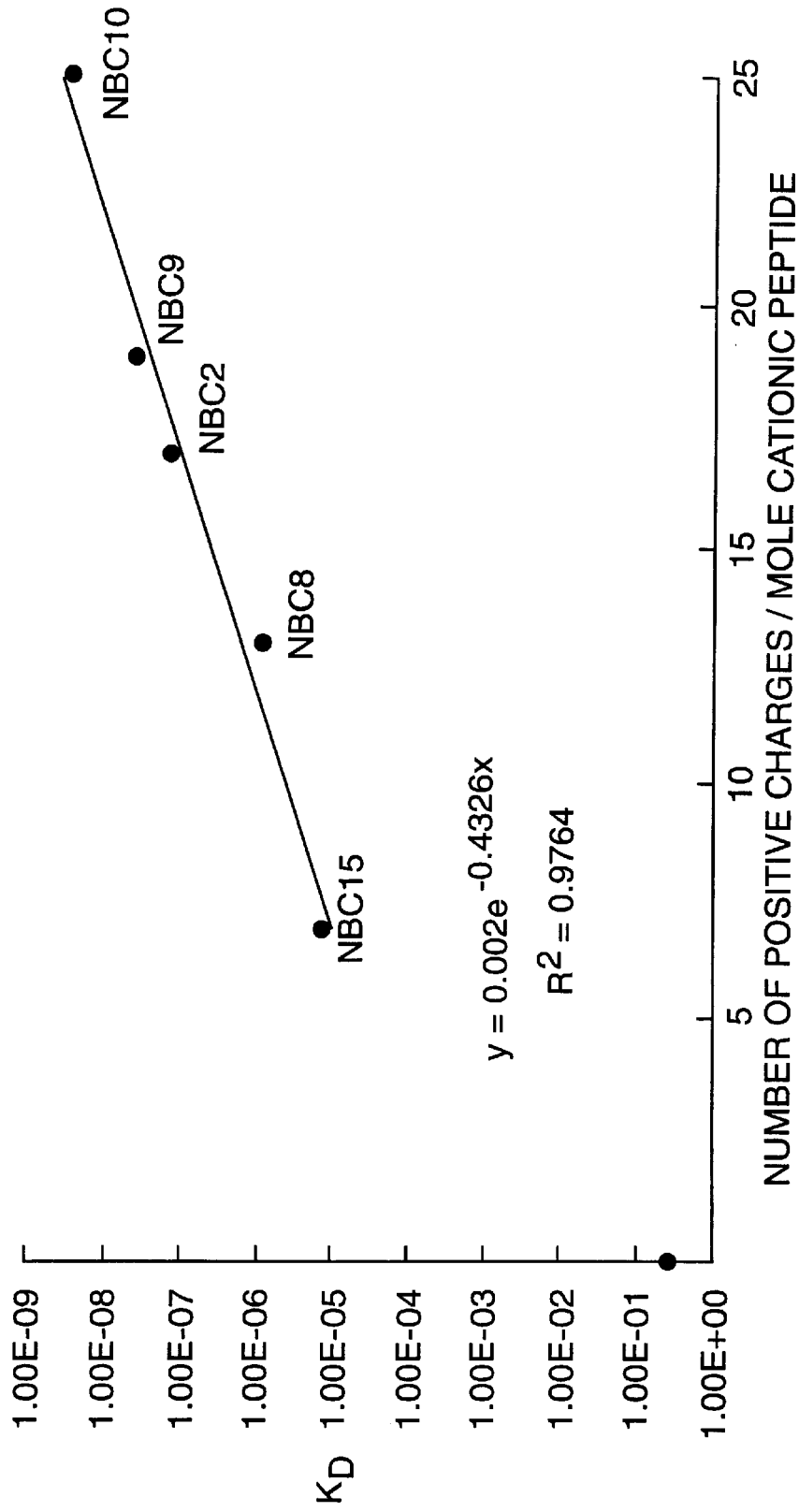
FIG. 4 PREDICTION OF RELATIVE BINDING AFFINITY OF CATIONIC PEPTIDES (NBC9 SERIES)

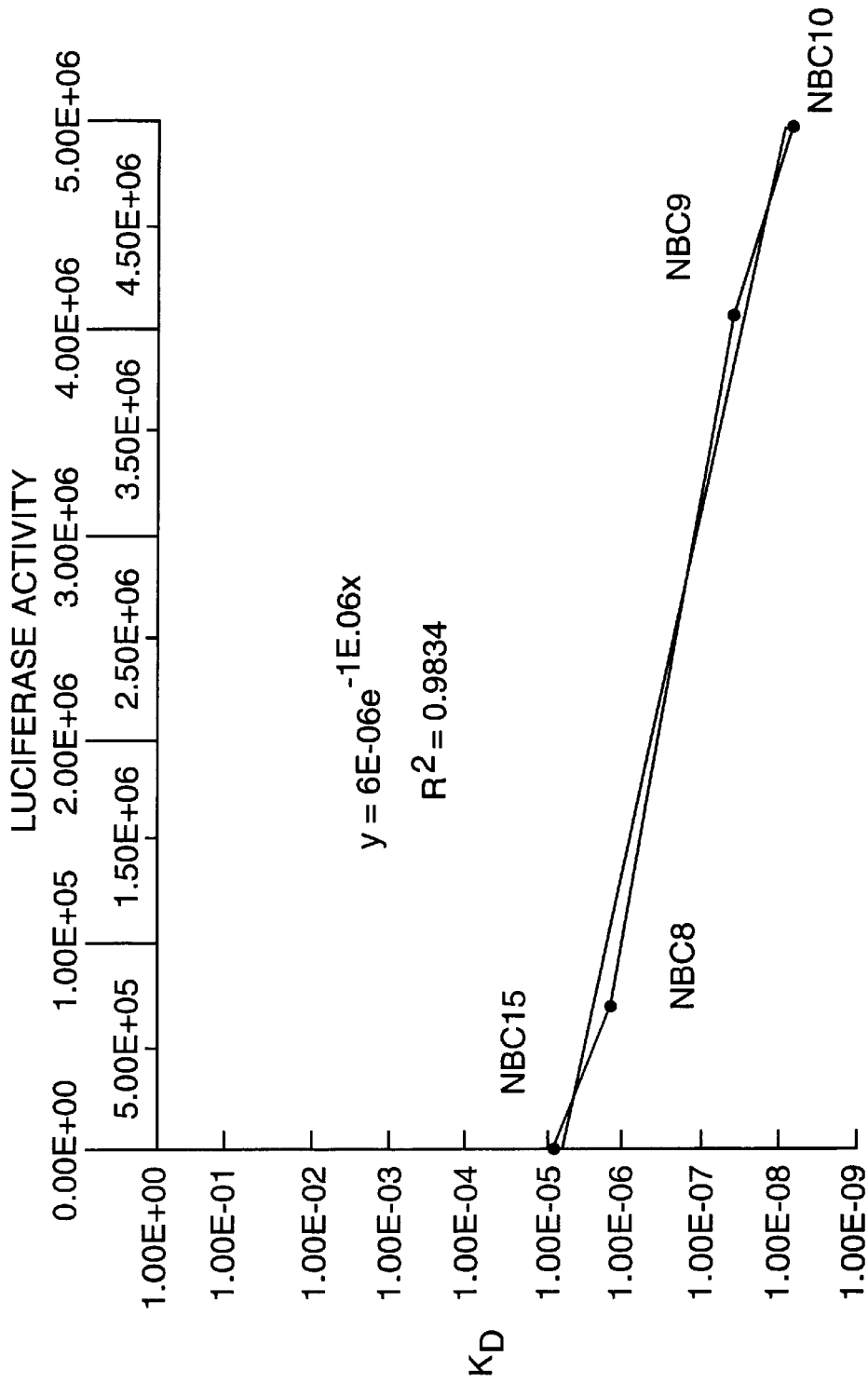

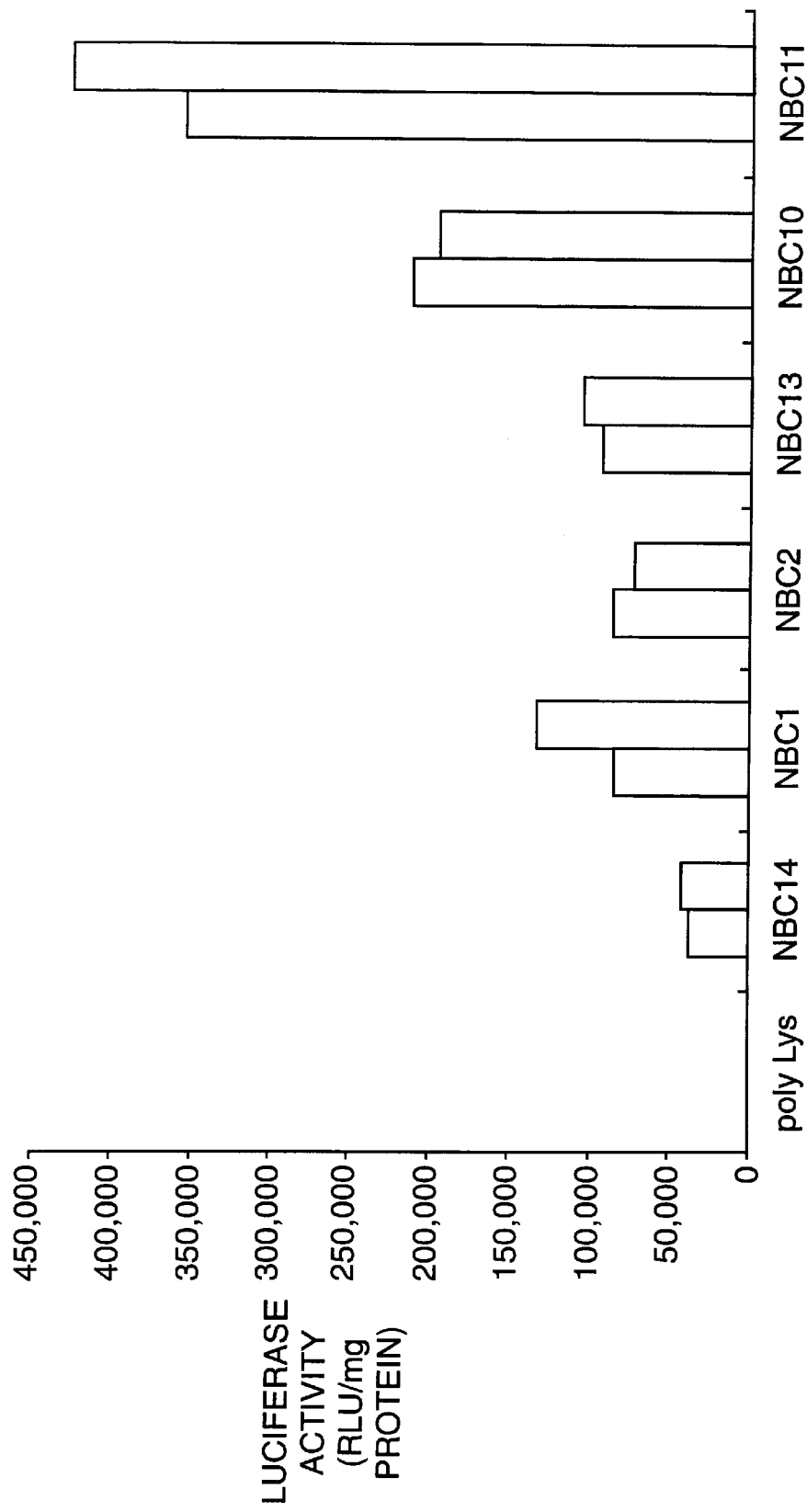
FIG. 7 RELATIVE TRANSFECTION EFFICIENCY OF CATIONIC PEPTIDES OF LOW POLYDISPERSITY COMPARED WITH POLY-LYSINE (NOMINAL SIZE 250 RESIDUES)

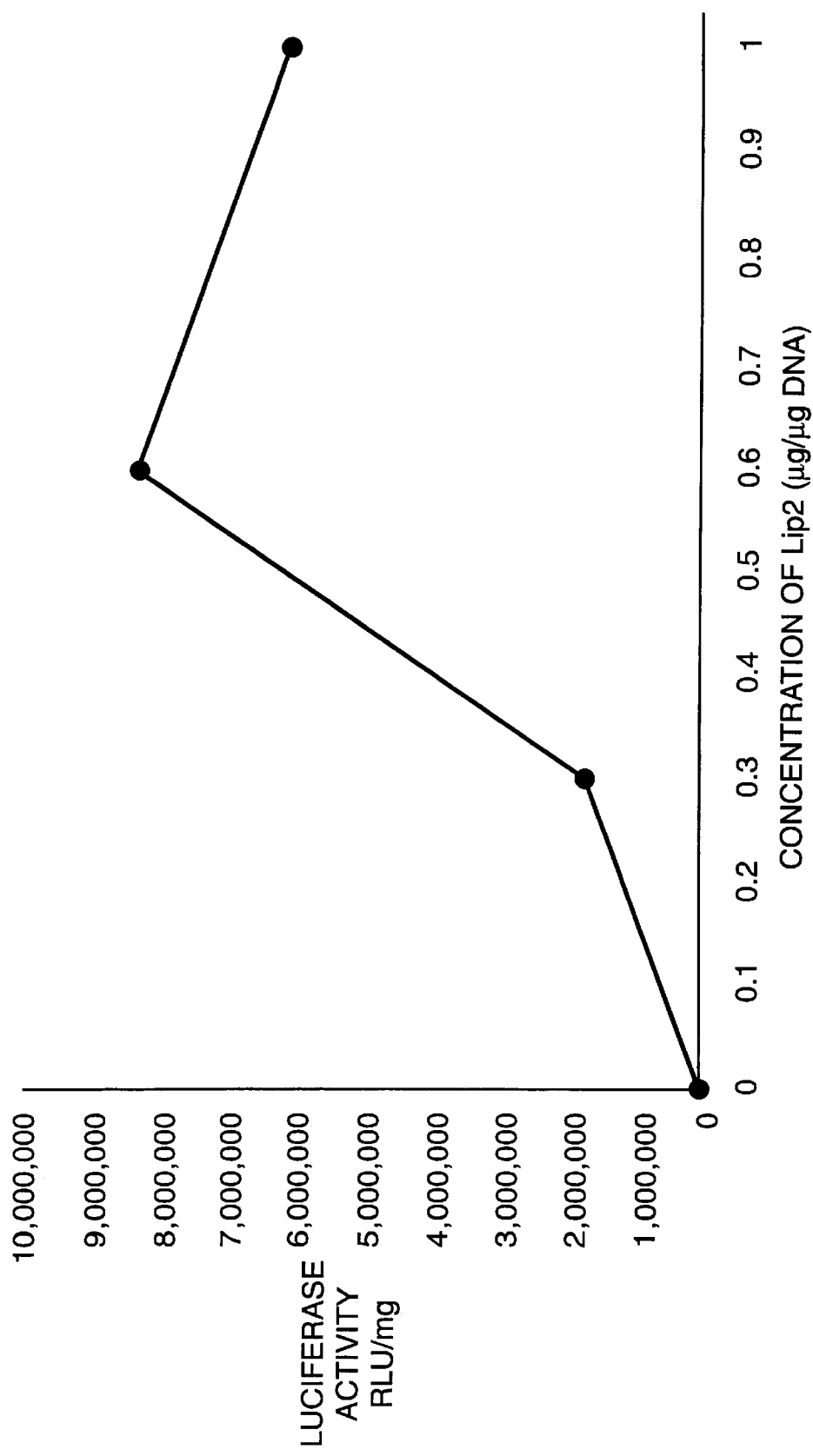

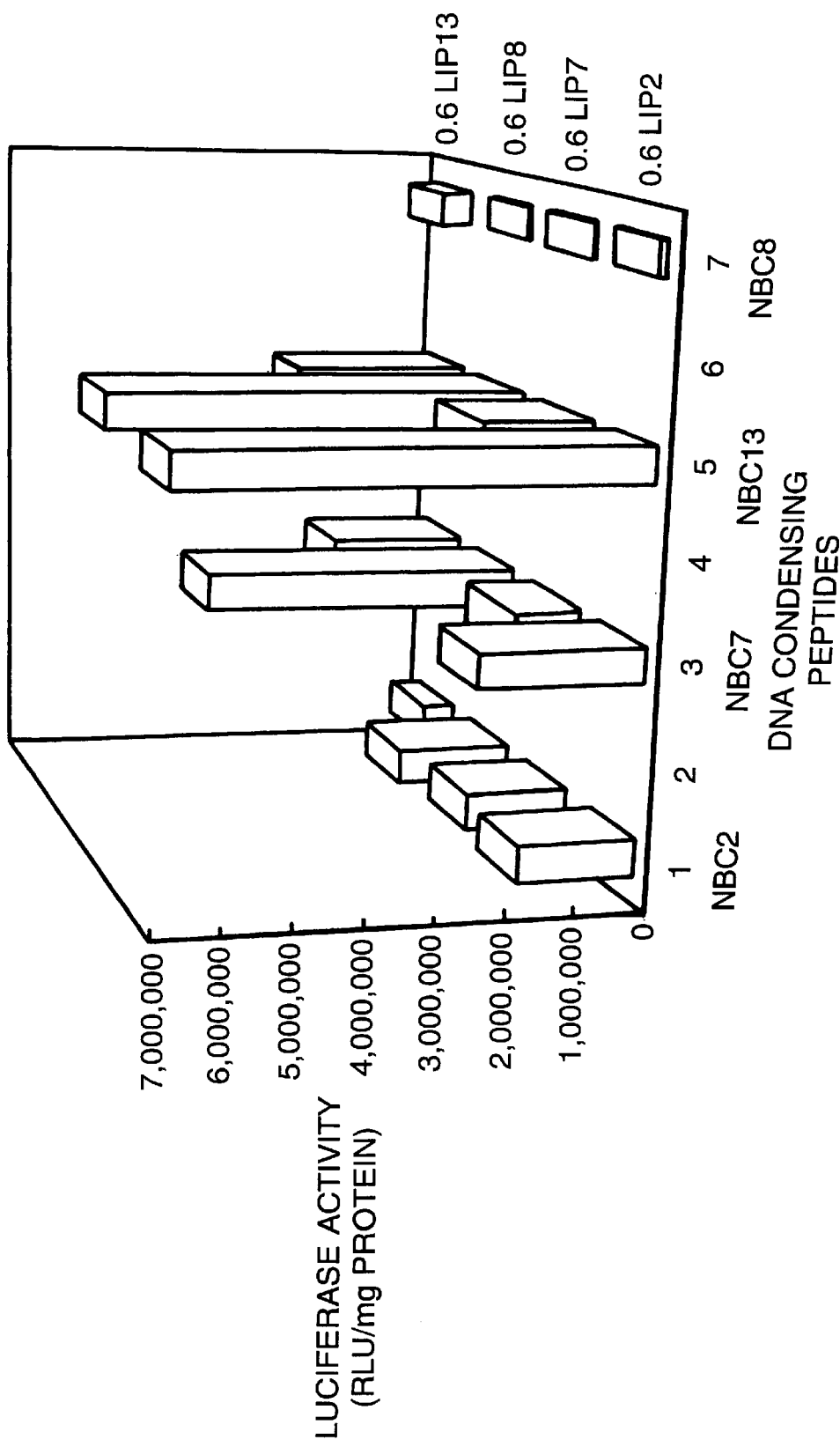
FIG. 9 EFFECT OF PEPTIDE STRUCTURE ON TRANSFECTION EFFICIENCY IN THE PRESENCE OF DIFFERENT LIPIDATED PEPTIDES

OPTIMIZATION OF GENE DELIVERY AND GENE DELIVERY SYSTEM

REFERENCE TO RELATED APPLICATIONS

This application claims priority under 35 U.S.C. §119(e) to U.S. provisional application 60/033,908 filed Dec. 23, 1996, incorporated herein by reference in its entirety.

FIELD OF THE INVENTION

This invention is generally in the field of DNA delivery systems. More specifically, this invention describes methods of optimizing the efficiency of transfecting cells with a DNA molecule bound to peptides and derivatives thereof.

All publications cited in this specification are incorporated herein by reference.

BACKGROUND OF THE INVENTION

Transfection of cells, whether in vitro, ex vivo or in vivo, involves not only delivery of the transfecting DNA to the cell nucleus, but also expression of the delivered DNA in the cell. Some gene delivery systems involve transfection of cells using a delivery complex in which DNA is condensed with cationic polymers such as cationic lipids or polylysine (see, for example, Cotten and Wagner (1993) Curr. Opin. Biotech., 4: 705). There is a need in the art for a gene delivery system which is stable in the bloodstream, targetable to selected tissue types, and capable of efficient transport into the cytoplasm and to the nucleus of both dividing and non-dividing cells. Some transfection techniques demonstrate that the transfecting DNA may be absorbed by cells, only to accumulate unchanged in the cytoplasm and unexpressed in the nucleus (for example, see Zaubner et al., (1995) J. Biol. Chem. 270: 18997, wherein cationic liposomes carrying DNA accumulate in the cytoplasm), suggesting that there is a need in the art for improvements in current methods of cell transfection.

SUMMARY OF THE INVENTION

This invention provides methods of screening of polyvalent cationic peptides, or derivatives of peptides (also called conjugates), for the ability to optimally transfect cells with a nucleic acid molecule condensed on the cationic peptide or conjugate based on determining the equilibrium dissociation constant (also called the equilibrium constant), $K_D$ or the apparent dissociation constant (also called the apparent dissociation constant), $k_d$, for the interaction between the peptide or conjugate and the nucleic acid molecule.

The invention is based on the recognition that the equilibrium constant for the interaction between a peptide, or derivative thereof, and a nucleic acid molecule is readily determined by measuring the change in surface plasmon resonance (SPR) signal caused by a bimolecular interaction between the nucleic acid molecule which is immobilized on a metal sensor chip, and the peptide or conjugate which is present in a solution flowing over the chip, and that the equilibrium constant, or simply the apparent dissociation constant, is a critical predictor of optimal transfection efficiency.

As used herein, the terms "optimal transfection" or "optimally transfect" refers to obtaining the largest number of transfected cells per unit amount of nucleic acid condensed on a particular peptide or conjugate of a gene delivery complex. It will be appreciated by one of skill in the art that the proportion of transfected cells will vary for each target cell and therefore the largest number of transfected cells in a given target cell population may be. for example, 25% or 50% of the targeted cells for one selected cell population, and may be 80% or even as high as 95% for another selected cell population. It will become apparent from the specification below that "transfection" is meaningful only in terms of expression of the nucleic acid in the host cell, and thus "expression" refers to the biological activity of the nucleic acid delivered to the host cell, whether that biological activity be the production of a gene product such as a protein or an RNA, or via a measurable biological effect of the nucleic acid in the host cell.

The nucleic acid to be delivered to the host cell need not be identical in length or composition to the nucleic acid immobilized on the sensor chip. It is preferred that the nucleic acid to be delivered and the chip immobilized nucleic acid possess the same overall properties as to DNA or RNA and as to strandedness (double or single-stranded). It also is preferred that the overall lengths of the delivered and immobilized nucleic acids be approximately the same; that is, if the nucleic acid to be delivered is about 50 nucleotides in length, the immobilized nucleic acid be in the range of 10–500 nucleotides in length; if the nucleic acid to be delivered is about 1.0 kb in length, the immobilized nucleic acid be in the range of 1.0 kb–10 kb in length; if the nucleic acid to be delivered is about 50 kb in length, the immobilized nucleic acid be in the range of 10 kb–100 kb in length.

The nucleic acid molecule immobilized on the sensor ship may be a DNA or an RNA, although DNA is preferred, and it may be a double-stranded or single-stranded nucleic acid molecule. The immobilized nucleic acid may be of any desired length (e.g. generally in the range of 10 nucleotides—1 kb–50 kb), and may be of any sequence composition.

In a preferred embodiment of the methods described herein, the nucleic acid molecule immobilized on the sensor chip is a double-stranded DNA which is a plasmid. Plasmid refers to a circular or linear form of double-stranded DNA which is large enough to contain a gene (that is, a sequence comprising coding as well as regulatory regions).

The invention thus encompasses a method of screening test peptides for the ability to optimally transfect cells with a nucleic acid molecule comprising detecting a change in the surface plasmon resonance of a nucleic acid immobilized on a sensor chip and exposed to a solution of a test peptide, wherein the change in surface plasmon resonance occurs upon binding of the peptide to and dissociation of the peptide from the immobilized nucleic acid, thereby to permit either calculation of the equilibrium dissociation constant $K_D$ or apparent dissociation constant, $k_d$; and (b) selecting the peptide having an equilibrium dissociation constant, $K_D$, with a value of approximately $1 \times 10^{-12}$ to $1 \times 10^{-6}$ (or apparent dissociation constant, $k_d$, with a value of approximately $1 \times 10^{-6}$ to $1 \times 10^{-1}$).

The invention also encompasses a method of screening test peptides for the ability to optimally transfect cells with a nucleic acid molecule comprising (a) detecting a change in the surface plasmon resonance of a nucleic acid immobilized on a sensor chip and exposed to (a) a solution containing a test peptide for a time sufficient to permit binding of the peptide to the immobilized nucleic acid followed by (b) a solution lacking test peptide for a time sufficient to permit dissociation of the peptide from the immobilized nucleic acid, wherein the change in surface plasmon resonance occurs upon binding of the peptide to and dissociation of the peptide from the immobilized nucleic acid, thereby to permit calculation of the equilibrium dissociation constant $K_D$; and selecting a peptide having an equilibrium dissociation constant, $K_D$, with a value of approximately $1\times10^{-12}$ to $1\times10^{-6}$.

The invention also encompasses a method of screening test peptides for the ability to optimally transfect cells with a nucleic acid molecule comprising (i) detecting a change in the surface plasmon resonance of a nucleic acid immobilized on a sensor chip and exposed to (a) a solution containing a test peptide for a time sufficient to permit binding of the peptide to the immobilized nucleic acid followed by (b) a solution lacking test peptide for a time sufficient to permit dissociation of the peptide from the immobilized nucleic acid, wherein the detection detects a change in surface plasmon resonance which occurs upon dissociation of the peptide from the immobilized nucleic acid, thereby to permit calculation of the apparent dissociation constant, $k_d$; and (ii) selecting a peptide having an apparent dissociation constant, $k_d$, with a value of approximately $1\times10^{-6}$ to $1\times10^{-1}$).

In preferred embodiments of the invention, the methods further comprise, prior to the detecting step, the steps of immobilizing the nucleic acid on a sensor chip; and exposing the immobilized nucleic acid molecule to a solution of a test peptide; and, optionally, the step of recording the change in surface plasmon resonance.

The invention also encompasses a method of screening test peptides for the ability to optimally transfect cells with a nucleic acid molecule comprisng (a) immobilizing the nucleic acid on a sensor chip; (b) exposing the immobilized nucleic acid molecule to a solution of a test peptide; (c) detecting and recording a change in the surface plasmon resonance upon binding of the peptide to the immobilized nucleic acid; (d) calculating the equilibrium dissociation constant $K_D$ (or apparent dissociation constant, $k_d$) of the test peptide from the recorded change in surface plasmon resonance; and (e) selecting the peptide having an equilibrium dissociation constant, $K_D$, with a value of approximately $1\times10^{-12}$ to $1\times10^{-6}$). (or apparent dissociation constant, $k_d$, with a value of approximately $1\times10^{-6}$ to $1\times10^{-1}$).

The invention also encompasses a method of transfecting cells with nucleic acid comprising the step of providing a nucleic acid condensing peptide/condensed nucleic acid complex, wherein a peptide of the complex has an equilibrium dissociation constant, $K_D$, with a value of approximately $1\times10^{-12}$ to $1\times10^{-6}$, or an apparent dissociation constant, $k_d$, with a value of approximately $1\times10^{-6}$ to $3\times10^{-3}$, or an apparent dissociation constant, $k_d$, with a value of approximately $1\times10^{-2}$ to $1\times10^{-1}$.

The invention also encompasses a method of transfecting cells with nucleic acid comprising delivering to the cell a nucleic acid condensing peptide/nucleic acid complex wherein a peptide of the complex has an apparent dissociation constant, $k_d$, with a value of approximately $1\times10^{-6}$ to $3\times10^{-3}$ or an apparent dissociation constant, $k_d$, is approximately $1\times10^{-2}$ to $3\times10^{-1}$.

The invention also encompasses a method of measuring the equilibrium constant, $K_D$ (or apparent dissociation constant, $k_d$) for a peptide binding to plasmid nucleic acid comprising (a) immobilizing the plasmid nucleic acid on a sensor chip; (b) exposing the immobilized nucleic acid molecule to a solution of a test peptide; (c) detecting and recording a change in the surface plasmon resonance upon binding of the peptide to the immobilized nucleic acid; and (d) calculating the equilibrium constant $K_D$ (or apparent dissociation constant, $k_d$) of the test peptide from the recorded change in surface plasmon resonance.

The invention also encompasses improvements upon a method of delivering a recombinant nucleic acid to a population of host cells, the improvement comprising obtaining optimal transfection of the cells by determining the equilibrium constant $K_D$ of a peptide that is present in a complex comprising a nucleic acid condensing peptide and a condensed nucleic acid for transfection from a change in surface plasmon resonance which occurs upon binding of the peptide to and dissociation of the peptide from an immobilized nucleic acid, or wherein the improvement comprises obtaining optimal transfection of the cells by determining the apparent dissociation constant, $k_d$ of a peptide that is present in a complex comprising a nucleic acid condensing peptide and a condensed nucleic acid for transfection from a change in surface plasmon resonance which occurs upon dissociation of the peptide from an immobilized nucleic acid In the above improvements, the methods may further comprise selecting an equilibrium rate constant, $K_D$, with a value of approximately $1\times10^{-12}$ to $1\times10^{-6}$ or apparent dissociation constant, $k_d$, with a value of approximately $1\times10^{-6}$ to $3\times10^{-3}$.

In a preferred embodiment, the screening methods of this invention comprise the additional step of selecting peptides or conjugates for transfection having an apparent dissociation constant, $k_d$, in the range of approximately $1\times10^{-4}$ to $1\times10^{-2}$ sec$^{-1}$ or an equilibrium constant, $K_D$, in the range of approximately $1\times10^{-9}$ to $1\times10^{-2}$ mol$^{-1}$.

In a more preferred embodiment, the screening methods of this invention comprise the additional step of selecting peptides or non-lipid conjugates for transfection having an apparent dissociation constant, $k_d$, in the range of approximately $1\times10^{-4}$ to $1\times10^{-2}$ sec$^{-1}$ or an equilibrium constant, $K_D$, in the range of approximately $1\times10^{-9}$ to $1\times10^{-8}$ mol$^{-1}$ for use in vivo transfections where it is important that decondensation of the nucleic acid from the peptide or conjugate does not occur as the nucleic acid-peptide or nucleic acid-conjugate complex is diluted, such as when injected into the blood stream. For ex vivo transfection using lipid conjugates, the highest transfection efficiency is using lipopeptides having $K_D$'s in the range of $1\times10^{-5}$ to $1\times10^{-7}$ (or $k_d$'s of $1\times10^{-3}$ to $1\times10^{-2}$).

In another more preferred embodiment of the invention, the screening methods of this invention comprise selecting peptides or conjugates for transfection having an apparent dissociation constant, $k_d$, of approximately $1\times10^{-2}$ sec$^{-1}$ or an equilibrium constant, $K_D$, of approximately $1\times10^{-6}$ mol$^{-1}$ for use in in vivo transfections where the nucleic acid-peptide or nucleic acid-conjugate complexes are administered directly to a localized area of tissue, such as a tumor.

This invention also provides a method of determining the apparent dissociation constant, $k_d$, or the equilibrium dissociation constant, $K_D$, for a peptide or conjugate binding to or complexing with plasmid nucleic acid comprising immobilizing the plasmid nucleic acid on a metal sensor chip, exposing the immobilized plasmid nucleic acid molecule to a solution containing a peptide or conjugate, detecting and recording a change in the surface plasmon resonance of the peptide or conjugate-nucleic acid interaction, and calculating the apparent dissociation constant, $k_d$, or the equilibrium dissociation constant, $K_D$.

The invention also encompasses a composition of matter comprising a sensogram (i.e., data which is rendered in tangible form such as on a piece of paper) in which the Y axis of the sensogram corresponds to resonance units and the X axis corresponds to time and the data line corresponds to a recording over time of a detected change in surface plasmon resonance of a bimolecular interaction between a nucleic acid molecule and a peptide or conjugate.

The invention also encompasses a sensogram in which the Y axis of the sensogram corresponds to resonance units and the X axis corresponds to time and the data line corresponds to detecting a change in the surface plasmon resonance of a nucleic acid immobilized on a sensor chip and exposed to a solution of a test peptide, wherein the change in surface plasmon resonance occurs upon binding of the peptide to and dissociation of the peptide from the immobilized nucleic acid.

This invention permits selection of peptides having sufficient binding capacity for nucleic acid to provide a gene delivery complex that is stable in the bloodstream, targetable to selected tissue types, and capable of efficient transport into the cytoplasm and to the nucleus. These requirements are met by selecting peptides based on their equilibrium constants as taught herein. The invention thus permits one of skill in the art to provide a condensing peptide/condensed nucleic acid complex wherein a proportion of the nucleic acid condensing peptides have linked thereto a selected functional group such as a cell targeting ligand, a cell import sequence, or a nuclear import sequence.

Further features and advantages of the invention will become more fully apparent in the following description of the embodiments and drawings thereof, and from the claims.

BRIEF DESCRIPTION OF THE DRAWINGS

FIG. 2 is a sensogram for the interaction of the peptide NBC11 with plasmid nucleic acid pRSVluc.

FIG. 3 is a sensogram for the interaction of the Lip9 conjugate with plasmid nucleic acid pRSVluc.

FIG. 4 is a graph of equilibrium dissociation constant, $K_D$, versus the number of positive charges per mole of peptide for plasmid pRSVLuc nucleic acid.

FIG. 5 is a graph of equilibrium constant versus luciferase activity of cells transfected with plasmid pRSVLuc nucleic acid complexed with NBC9 series peptides.

FIG. 6A shows the results of transfection of Mouse KLN205 Tumour with plasmid pTXO118 complexed with 0.5 $\mu$g NBC15 peptide/$\mu$g DNA. FIG. 6B shows the results of transfection of Mouse KLN205 Tumour with plasmid pTXO 118 complexed with 0.5 $\mu$g NBC9 peptide/$\mu$g DNA.

FIG. 7 shows the relative transfection efficiency of individual NBC peptides and polylysine peptides.

FIG. 8 is a graph showing the effect of the presence of lipidated nucleic acid condensing peptide on the transfection efficiency of a gene delivery system as described herein.

FIG. 9 shows the transfection efficiency of complexes wherein the nature of the lipidated peptide was varied in complexes made up of 0.6 $\mu$g lipidated peptide/2 $\mu$g free.

DETAILED DESCRIPTION

Figure 1:
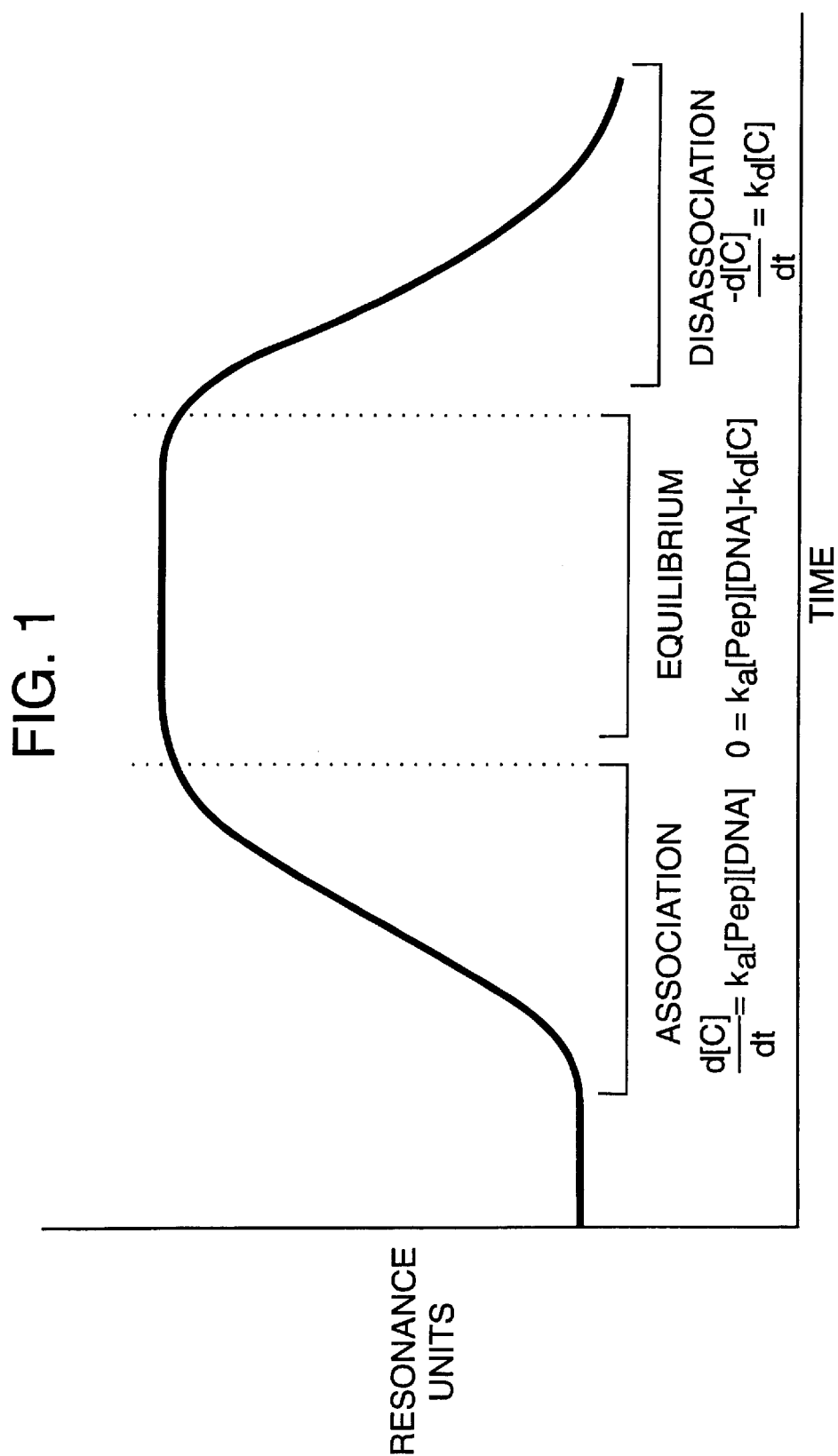
FIG. 1 is a diagram of a theoretical sensorgram of resonance units (RU) versus time of a bimolecular interaction between a nucleic acid molecule and a peptide or conjugate, the three characterisitic regions of the sensogram, and a mathetical equation describing each of the three regions.

This invention provides methods of screening peptides for the ability to optimally transfect cells with a gene or other nucleic acid molecule. Such peptides can be used as the peptide component of an efficient non-viral gene delivery system useful in in vitro, ex vivo, or in vivo methods of gene delivery, such as in gene therapy.

Without being bound to any one theory, it is believed that, in gene delivery systems in which cationic polymers are used to condense nucleic acid, decondensation of the delivered nucleic acid either in the cytoplasm or in the nucleoplasm is necessary for its efficient expression. Those cationic polymers which have too great an avidity for the delivered nucleic acid often result in an unacceptably low level of gene expression, suggesting that decondensation of the nucleic acid does not occur. Without decondensation of the delivered nucleic acid, successful transfection (i.e., transfer of the nucleic acid to the nucleus result in its expression) of a significant number of cells is thwarted. Control of decondensation is therefore an important parameter to consider in the design of gene delivery systems in order to achieve optimal levels of successful transfection, that is levels of transfection provide for clinically or diagnostically useful levels of transfection in a target cell population. "Useful" levels of transfection are determined by the clinician or diagnostian for a given disease or disease parameter, and thus are determined by one of skill in the art for a given nucleic acid, a given target cell, and a given disease.

There is a need, therefore, for methods of optimizing decondensation of nucleic acid molecules from a gene delivery system in order to optimize the efficiency with which cells are transfected with a particular nucleic acid molecule used in a gene therapy to treat the cells.

The basis for the screening methods described herein is the discovery that certain kinetic constants that describe the bimolecular interaction between a peptide and a nucleic acid molecule can be used to predict whether a particular peptide can enhance transfection of cells with a nucleic acid molecule relative to other peptides. That is, a nucleic acid condensing peptide/nucleic acid delivery complex may comprise peptides having different amino acid compositions, and therefore different affinities for the nucleic acid and/or different functional groups attached to the peptide, and therefore different affinities for the nucleic acid. In this sense, not all of the peptides in the delivery complex will have equal affinity for the nucleic acid being delivered. For example, a given complex may comprise a nucleic acid condensed with a first peptide having a hydrophilic coatings to promote evasion of the reticular endothelial system, a second peptide targeting endosome escape functions, a third peptide having a nuclear import sequence, and a fourth peptide having no functional group attached. The first and second peptides are useful for entering the cell and cell cytoplasm, but are not required once the complex has entered the cytoplasm. The third peptide is useful for entering the nucleus, but is not required after nuclear entry. The fourth peptide is useful throughout the cell targeting and entry process, and ultimately must be released upon decondensation of the nucleic acid in the cell nucleus. In the simplest embodiment of this example, the four peptides will have the same amino acid sequence, but will differ in affinities for the nucleic acid by virtue of the functional group attached to the peptide. In other possible embodiments of this example, the four peptides may have different amino acid sequences, thereby providing for additional variations in affinities for the nucleic acid to be delivered.

A critical factor in determining whether a first peptide-nucleic acid complex will transfect cells better than a second complex is the ability of the peptide component of the complex to release from the condensed nucleic acid component, i.e., thereby to promote decondensation, at an appropriate cellular location (either the cytoplasm or the nucleoplasm) for the particular nucleic acid to be expressed. In order to optimize both decondensation of the nucleic acid component at the intended site of gene expression and the selective shedding of peptide components of the gene delivery complex prior to transport to the intended site of gene expression, an accurate measure of the affinity of the peptide component for the nucleic acid is required.

As used herein, the term "conjugate" refers to a derivative of a peptide which contains additional functional groups that are covalently linked or conjugated to a core peptide. Such functional groups may enhance the nucleic acid condensing or decondensing ability of the core peptide or enhance the transport and delivery of the nucleic acid-peptide complex to the appropriate cellular location for subsequent decondensation and transcription of the nucleic acid component of the complex. Examples of such functional groups include lipids (see below). It is understood that in the discussion below and unless indicated otherwise, the term "peptide component" encompasses the use of conjugates in a gene delivery system and that the term "peptide-nucleic acid complex" includes conjugate-nucleic acid complexes as well.

Surface Plasmon Resonance

Surface plasmon resonance (SPR) has been used in the prior art to measure biomolecular interactions. Typically, one component is immobilized on a metal coated sensor chip and a second component is contained in a solution flowing over the chip. Binding of the second component to the component immobilized on the chip results in a change in the angle of non-reflectance (resonance angle) of a light beam shining on the chip This change in resonance angle can be monitored in real time using a biosensor-based device such as the BIAcore (Pharmacia Biosensor AB, Uppsala, Sweden) and thus, the interaction and binding characteristics of the two components can be analyzed (see, for example, L öfas et al., (1990) J. Chem. Soc., Chem. Commun., 21: 1526–1528; Fisher et al., (1994) Protein Sci., 3: 257–266). Several workers have shown the utility of SPR in the study of protein-oligonucleotide interactions (Jost et al., (1991) Nucleic Acids Res., 19: 2788; Bondeson et al., (1993) Anal. Biochem. 214: 245; Fisher et al., (1994) Protein Science, 3: 257–266; Parson et al., Nucleic Acids Res. 23: 211; Hadfield et al., (1995) Nucleic Acids Res., 23: 995; Janscak et al., (1996) J. Mol. Biol. 257: 977). In these studies, biotinylated oligonucleotides were immobilized to a streptavidin-coated chip and a protein solution applied to that chip.

Surface Plasmon Resonance as a Tool in the Design of Gene Delivery Systems

According to the methods of this invention, reproducible data can also be obtained on the binding of cationic peptides to immobilized nucleic acid. Also, conditions required for complete dissociation of a peptide from the nucleic acid can be determined. According to the invention, different peptides are ranked in order of their avidity for nucleic acid as determined by the equilibrium dissociation constant, $K_D$, or the apparent dissociation constant, $k_d$, calculated from the SPR measurements using a biosensor-based device, such as the BIAcore. Such a ranking is directly correlated with the ability of each peptide to efficiently transfect cells with the nucleic acid.

In the examples described below, SPR was detected using the BIAcore system. This machine contained an SPR detector and an integrated microfluidic cartridge which is engineered such that an analyte solution (cationic peptide) is continuously passed over the sensor chip. The sensor chip consists of a glass plate coated with a thin film of gold covered in a layer of carboyxymethyl dextran. The chip used has a dextran layer to which streptavidin is covalently attached. The chip is prepared for use by adding biotinylated nucleic acid which will be bound to the chip via the streptavidin-biotin interaction, and the same chip is used in a series of experiments.

As material binds to the immobilized nucleic acid molecule on the sensor chip, the SPR angle of plane polarized light shining on the surface of the chip is monitored by the detector. Changes in angle are defined as resonance units (RU) and data are collected every second. Background effects are detected and automatically subtracted by the use of a control flow cell in line with the nucleic acid flow cell.

Conventionally the data is displayed as a sensorgram which plots the change in signal with time. A typical sensorgram has three phases: an association phase, an equilibrium phase and a dissociation phase (see FIG. 1). The rise in signal occurs as more peptide binds to the immobilized plasmid DNA until equilibrium conditions are reached. The height of the peak is directly proportional to the mass of peptide bound. If the flow continues with buffer containing no peptide, peptide begins to dissociate from the complex and the resonance signal is reduced. The sensorgram can be used to compute apparent rate constants for each of the three individual processes.

The reaction between the immobilized plasmid DNA can be assumed to follow pseudo first order kinetics:

(1) $dC/dt = k_a[P_F][P_{max}-P_B] - k_d[P_B]$ where $dC/dt$ is the rate of complex formation, $[P_F]$ is the concentration of peptide in free solution, $P_{max}$ is the maximum capacity for peptide binding, $P_B$ is the amount of bound peptide, $k_a$ is the apparent rate constant for association, $k_d$ is the apparent rate constant for dissociation.

At equilibrium, $$0 = k_a[P_F][P_{max} - P_B] - k_d[P_B] \qquad (2)$$

$$k_a[P_F][P_{max} - P_B] = k_d[P_B]$$

$$\frac{[P_F][P_{max} - P_B]}{[P_B]} = \frac{k_d}{k_a} = K_D$$

Equation 2 shows that the equilibrium rate constant, $K_D$, can also be calculated from these data NBC2, NBC10, NBC9, NBC8, NBC15, NBC7, NBC11 and polylysine (PolyK) of average chain length of 123 lysine residues have been studied in detail. The basic structures of the NBC peptides is described above. NBC2 is a peptide containing three sequence motifs based on Histone H1. NBC15, NBC8, NBC9 and NBC10 contain 1, 2, 3 and 4 sequence repeats derived from Histone H1. NBC7 and NBC11 are, respectively, arginine rich and lysine rich peptides designed to form α-helical structures which will interact with the major groove of the DNA helix. With the exception of NBC7 and NBC11, the pseudo-first order rate constants for the association reaction, i.e., the "on rate", are directly proportional to molecular weight. In the case of NBC7 and NBC 11 the association reaction is more complex with clear biphasic kinetics (FIG. 2). A fraction of the peptide associates with nucleic acid with a higher binding rate and a fraction with a lower rate.

Dissociation rates, the "off rate", decrease with increasing molecular size.

TABLE 1

| Peptide | ka (sec-1) | kd (sec-1) | t½ (sec) | $K_D$ (M) |
|---|---|---|---|---|
| NBC15 | $7.12 \times 10^3$ | 0.0572 | 12 | $8.0318 \times 10^{-6}$ |
| NBC8 | $5.00 \times 10^4$ | 0.06248333 | 11 | $1.2497 \times 10^{-6}$ |
| NBC9 | $9.78 \times 10^4$ | $2.93 \times 10^{-3}$ | 236 | $2.9908 \times 10^{-8}$ |
| NBC10 | $2.19 \times 10^5$ | $1.10 \times 10^{-3}$ | 628 | $5.0183 \times 10^{-9}$ |
| NBC2 | $1.02 \times 10^5$ | $9.38 \times 10^{-3}$ | 74 | $9.1983 \times 10^{-8}$ |
| NBC14 | $2.11 \times 10^5$ | $7.50 \times 10^{-4}$ | 920 | $3.5598 \times 10^{-9}$ |
| NBC7 | $3.67 \times 10^3$ | $1.33 \times 10^{-4}$ | 5188 | $3.6273 \times 10^{-8}$ |
| NBC11 | $2.07 \times 10^4$ | $1.61 \times 10^{-4}$ | 4286 | $7.7653 \times 10^{-9}$ |
| Lip9 | 75850 | 0.000474 | 1456 | $6.2492 \times 10^{-9}$ |
| InsIa | $6.85 \times 10^4$ | $5.41 \times 10^{-4}$ | 1275 | $7.9027 \times 10^{-9}$ |
| InsII | $5.26 \times 10^4$ | $2.92 \times 10^{-4}$ | 2367 | $5.5471 \times 10^{-9}$ |
| InsPEG | $3.24 \times 10^4$ | $1.26 \times 10^{-3}$ | 549 | $3.8781 \times 10^{-8}$ |
| PolyK123 | $3.16 \times 10^5$ | $1.65 \times 10^{-6}$ | 418181 | $5.2215 \times 10^{-12}$ |

The equilibrium constant, $K_D$, is a measure of the relative affinity of the peptide for nucleic acid under equilibrium conditions. In general, for a related series of cationic peptides, $K_D$ decreases proportionally with increasing size.

It is clear from other experiments that lipidated complexes have much higher affinities for nucleic acid than the underivitized peptide. These lipidated peptides have such a high affinity for the sensor chip that a complete analysis has not yet been completed (FIG. 3). Although the "on rates" observed are similar to those seen for the free peptides. Dissociation is, however, extremely slow, suggesting extremely high affinity for nucleic acid.

Nucleic Acid Condensing Peptides Useful According to the Invention

A variety of peptides and their corresponding conjugates can be synthesized which have the ability to condense nucleic acid, such as DNA, and therefore, may be useful as a peptide component of a gene delivery system.

The sequence of the nucleic acid condensing peptide and whether it has one or more attached functional groups has a marked effect on transfection efficiency. Without being bound to any one theory, it is believed that transfection efficiency is partly dependent on the relative affinity of the nucleic acid condensing peptides for nucleic acid. It is believed that, unless nucleic acid binding affinity is relatively high, the complex will decondense too soon upon entry into the cell, e.g., in the cytoplasm of the cell, and be unavailable for nuclear import in the cell. It also is believed that if the binding affinity is too high, the complex will fail to decondense in the nucleus, and be unavailable for expression in the nucleus.

Nucleic acid condensing peptides useful in the invention possess the following characteristics.

1) Nucleic acid condensing peptides useful in the invention are characterized in that the peptides are heteropeptides.

As used herein, a "heteropeptide" refers to a peptide having a selected amino acid sequence. The term "heteropeptide" refers to a peptide having an amino acid composition of at least two different amino acids. This is in contrast to a "homolpeptide" in which the amino acid composition consists of identical amino acids. Thus, a homopeptide consists of 100% of the same amino acid, whereas a heteropeptide consists of a peptide chain in which as few as a single amino acid differs from the remainder of the amino acids in the chain, or, for example, 5%, 10%, 20%, 30%, 50%, 70%, 80%, 90%, etc., of the amino acids in a chain differ from the remaining amino acids in the chain. A heteropeptide is therefore a linear peptide consisting of, in terms of its selected amino acid sequence, a variety of (i.e., at least two, at least three, at least four, etc.,) types of amino acids.

As used herein, an "amino acid" refers to any of the twenty natural common amino acids, and also may refer to natural, uncommon amino acids or amino acid derivatives or analogs. An amino acid in D- or L- form may be present in a peptide according to the invention.

2) Nucleic acid condensing peptides of the invention are also characterized in that a plurality of nucleic acid condensing peptides or a preparation of nucleic acid condensing peptides useful in the invention has a low polydispersion index.

Nucleic acid condensing peptide preparations of the prior art, e.g., known as polycations, have a polydispersion index>1.1. This is evident in the description of polylysine peptide preparations in the prior art as having a "mean Mr" (Wu et al., (1987) J. Biol. Chem., 262: 4429; Wu et al., (1988) J. Biol. Chem., 263: 14621; and Wu et al., (1988) Biochem., 27: 887) or having "an average chain length" (Wagner et al., (1991) Proc. Nat. Acad. Sci., 88: 4255; Wagner et al., (1992) Proc. Nat. Acad. Sci., 89: 7934) or an "average degree of polymerization" (Birnsteil et al., EP 0 532 525). Polylysine preparations having a mean Mr or an average chain length are used in the prior art to condense DNA for gene delivery. Such preparations are disclosed as having an average degree of polymerization of a given number of lysine groups, e.g., "polylysine 90" has an average degree of polymerization of 90 lysine groups; "polylysine 190" has an average degree of polymerization of 190 lysine groups; etc (Birnsteil et al., supra.) Preparations of polylysine are available commercially from Sigma Corporation (St. Louis, Miss.) and are known by one of skill in the art and documented upon purchase to have an actual distribution of sizes within each sample which varies per sample, and may vary, for example, from 30%–150% of the material being distributed. Thus, the actual peptide length within such a sample may be, for example, 80% above or 80% below the stated average length of the peptide. The length of the peptide is thus reported as an average of various sizes which average is determined by low-angle light scattering analysis of individual lots of chemically synthesized peptide.

Nucleic acid condensing peptide preparations useful according to the invention have a low polydispersion index (PDI), also termed index of polydispersity. As used herein, a "low" polydispersion index refers to a PDI of <1.01. Nucleic acid condensing peptides useful in the invention have a PDI <1.01, and preferably have a PDI<1.001. Nucleic acid condensing peptide preparations of the invention, of course, may have a PDI of 1.0 and thus are termed "monodispersed". As used herein, a "high" polydispersion index refers to a PDI of >1.1,>1.2, >1.3, and generally in the range of 1.1–2.0.

The polydispersion index is used to characterize the molecular weight distribution of polymeric compounds. The PDI for a polymer having a homogeneous distribution of molecular weights (i.e., where the polymer preparation contains a uniform molecular weight) is 1.0, and for a highly heterogeneous polymer preparation (i.e., where the polymer preparation contains a wide distribution of molecular weights), the value approaches 2.0.

The polydispersion index of a peptide preparation may be determined according to two methods which are described below: 1) using light scattering and colligative properties of the peptide preparation to determine the weight and number average molecular weights of the peptides in a preparation; or 2) using electro-spray mass spectrometry to determine the molecular weights of peptides in a given preparation. It is critical to the invention that the PDI be calculated according to the most accurate of the two methods, i.e., electro-spray mass spectrometry. That is, the former method of calculating the PDI provides only a rough estimate of the PDI in that, for a given peptide preparation, the ratio of weight average molecular weight/number average molecular weight for heterogeneous polymers may be determined, respectively, by light scattering and from colligative properties of the peptide preparation (G. Odian in *Principles of Polymerisation*, John Wiley and Sons, (1981)). One such colligative property is viscosity (Odian, supra). However, these parameters for measuring weight and number average molecular weights, are not accurate enough to be used in the determination of the PDI of peptides having low polydispersion, because they provide only a rough estimate of the PDI, i.e., only to within 1% of the mass of each peptide component of the preparation.

For peptide preparations having a PDI<1.01, i.e., those peptide preparations synthesized according to methods described herein, a highly accurate measurement of peptide length in a peptide preparation must be provided such that the accuracy is within 0.01% of the mass of each peptide component of the preparation, and preferably within 0.001%.

The PDI for polymer peptides disclosed herein may be calculated from analysis of the peptides by electro-spray mass spectrometry. This method gives the exact mass of each component to within 0.001%. The PDI values of the peptide preparations useful in the present invention are in the range of 1.0–1.01. Peptide preparations which are especially useful in the invention possess a PDI<1.01, and even <1.001. In contrast, the PDI values for the nucleic acid condensing peptide preparations reported in the prior art are >1.1.

Calculation of Polydispersity Index of Synthetic Peptides

The polydispersion index is used to characterize the molecular weight distribution of polymeric compounds.

$$PDI = \frac{Mw}{Mn}$$

Where Mw is the weight average molecular weight and Mn is the number average molecular weight.

The usual method for determining the weight average molecular weight of heterogeneous polymers such as polylysine is to use light scattering where the amount of light scattered depends on molecular size as well as the number of complexes. In these cases the number average molecular weight is calculated from a colligative property of the polymer in solution such as viscosity since this property is dependent on the number of molecules of polymer per unit volume.

For example Poly-L-Lysine 25000; Sigma Product P7890, Lot No 93H-5516 has a PDI of 1.2. This result is typical for the batches of poly-lysine used in many gene transfer experiments reported in the literature.

For preparations of low polydispersity this approach cannot be used because of the relative inaccuracy of both viscosity and light scattering measurements. In these cases electrospray mass spectrometry may be used.

The deconvoluted electrospray mass spectrum of peptide NBC9 (theoretical mass 4082.2) was determined as follows. An aqueous solution of 1 mg/ml peptide was prepared and the sample diluted in a mixture of acetonitrile:methoxyethanol:0.1% trifluoroacetic acid. The experiment was performed on a VG Instruments Quattro II instrument fitted with a quadropole analyser. The instrument was calibrated with myoglobin and 10 µl aliquots were injected directly into the instrument source.

This technique gives the exact mass and by integrating the areas of each peak the relative proportions of each component can be estimated. This enables the Mw, Mn and Polydispersion Index to be calculated.

$$Mw = \frac{\Sigma ni\, Mi2}{\Sigma ni\, Mi};$$

$$Mn = \frac{\Sigma ni\, Mi}{\Sigma ni}$$

Integration of the peaks in the NBC9 spectrum gave the following relative areas:

| Mass | Area (ni) |
|------|-----------|
| 4212 | 120 |
| 4084 | 4250 |
| 4064 | 420 |
| 4013 | 900 |
| 3838 | 150 |

From this data using the formulae above, Mw=4070; Mn=4067; PDI=1.0008.

3) Amino acid length and composition of nucleic acid condensing peptides of the invention.

A nucleic acid condensing peptide suitable according to the invention is a basic peptide, i.e., a peptide with net positive charge, for example a peptide or polypeptide comprising 2–50. preferably 12–40, and more preferably 15–38 D- or L- amino acid residues. Preferably, the polypeptide includes at least 30%, more preferably 50%, and could include as much as 80–90% basic amino acids, such as lysine, arginine, histidine, ornithine or a non-natural amino acid containing a side chain having a secondary or tertiary amine group.

A nucleic acid condensing peptide according to the invention is preferably a peptide of, for example, 8–50 residues in length which includes a cysteine and/or threonine and/or serine residue which is available for regio-specific conjugation to a ligand, as defined herein. It is preferred that the cysteine and threonine residues be located N- and C-terminally, respectively, such that they may act as handles for covalent attachment of ligands.

Although the invention contemplates the use of heteropeptides having overall net positive charge, nucleic acid condensing peptides useful in the invention also include peptides wherein a large proportion (e.g., 30%–90%) of the amino acid composition of the peptide is a single basic amino acid species, such as lysine. For example, a heteropeptide which includes a sequence of from approximately 8 to approximately 30 lysyl residues is useful according to the invention. However, a peptide which is a homopolymer of lysyl residues is not useful according to the invention because homopolymeric polylysine tends to be cytotoxic and to stick nonspecifically to cell surfaces under certain conditions. Thus, the heteropolymeric nucleic acid condensing peptides contemplated herein are advantageous over homopolymers such as polylysine.

4) A preferred nucleic acid condensing peptide is a peptide or polypeptide having an alpha-helical (α-helical) conformation structure.

Such peptides, of which NBC7 and NBC11 (described herein) are specific examples, have been designed to interact with nucleic acid by interacting through a conformational structure that is alpha helical. Where a functional group is covalently linked to the peptide, it follows that the functional group of the conjugate may be positioned around the turn of the alpha helical structure so as to be optimally exposed to the outer surface of the nucleic acid-conjugate complex.

The above description focuses on the conformational structure of nucleic acid-peptide complexes (i.e., nucleic acid noncovalently associated with a peptide or a conjugate which includes a peptide of the invention covalently linked to a functional group). The relevant intermolecular interactions are refined by building a rigid scaffold which will specifically dock with nucleic acid and allow positioning of the functional moiety such that steric hindrance will not occur. Such a rigid scaffold is provided by any peptide which forms a stable α-helix.

A number of proteins that specifically interact with nucleic acid (e.g., P22 cro, repressor. trp repressor, Cap, etc.) interact through an α-helix structure (10 residue) which lays across the major groove of the nucleic acid helix. This a-helix is usually followed in the polypeptide by a reverse turn forming the helix-turn-helix motif which is characteristic of these proteins. Most of the interactions that these sequences make with the DNA are weak hydrogen bonds to the phosphate and bases. This is because the function of these domains is to recognize a particular base sequence and then trigger a conformational change. We hypothesized that if such helices are designed so that the hydrogen bonds were replaced by ionic interactions, the binding would be much stronger and useful as a docking/condensation peptide.

A peptide having an a-helical scaffold is designed as follows. Using a molecular model of a 10 residue a-helix, a helical wheel and a model of B-DNA it is apparent that strong interactions can be made using a repeating sequence motif of $X_1X_2$-BB-$X_1X_2$-BB-$X_1X_2$, where $X_1$ is a basic residue interacting with the phosphate on one side of the major groove and $X_2$ is a basic residue interacting with a phosphate diametrically opposite the other side of the major groove. Either of $X_1$ and $X_2$ may be, for example, lysine, arginine, or histidine. Lysine, arginine, and histidine are preferred because both amino acids 1) are of sufficient size to bridge the major groove gap, 2) will interact strongly with phosphate and 3) are strong helix formers. If the residues BB are also residues with strong helix-forming propensities then the peptide will form a stable α-helix in solution.

Preferred nucleic acid condensing peptides according to this aspect of the invention will fall within the generic formula

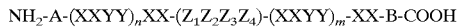

$\mathrm{NH_2\text{-}A\text{-}(XXYY)_n XX\text{-}(Z_1Z_2Z_3Z_4)\text{-}(XXYY)_m\text{-}XX\text{-}B\text{-}COOH}$ where X is a naturally occurring or synthetic amino acid carrying a positively charged group on the side chain such as lysine, arginine, 2,4-diamino-butyric acid, histidine, and ornithine or a non-natural amino acid containing a side chain having a secondary or tertiary amine group;

where Y is naturally occurring amino acid which has a high propensity to promote alpha helix formation as defined by Wilt and Thornton ((1988) J. Mol. Biol., 203: 2221–232) such as glutamic acid, alanine, leucine, methionine or glutamine, tryptophan or histidine;

where $Z_{1-4}$ are naturally occurring amino acids with at least 3 members of the sequence having a high propensity to form stabilized turn structures as defined by Wilt Thornton (loc. cit.) such as, asparagine, glycine, proline, serine, and aspartic acid;

where A is N-terminal serine or threonine allowing specific oxidation of the side chain to an aldehyde group with periodic acid and thereby permitting conjugation of the peptide to another molecule carrying a reactive hydrazide or aminooxyacetyl function;

where B is any amino acid but preferably alanine, glutamic acid or cysteine; and where n =2–4 and m=2.

It is also contemplated according to the invention that peptides useful in the invention may contain one or more internal serine, threonine, or cysteine residues, preferably at a position in the sequence which will be exposed for conjugation to a selected ligand, and thus not on the positively charged (DNA oriented) face of the α-helix. This positioning of selected reactive amino acid residues within the peptide and oriented such that they do not contact the face of the peptide that contacts DNA permits conjugation of the peptide with other functional peptides by bonds of selected and defined stability. Cysteine allows specific conjugation via the thiol side chain to compounds containing other reactive thiol groups (via disulfides), alkylating functions (to form thioether bonds), or other thiol reactive groups such as maleimide derivatives. Bonds of "defined stability" are described hereinbelow, and include bonds such as acid labile bonds (hydrazone) or linkages that are less stable in the reducing environment of the cytosol (disulfide). Such bonds are useful for carrying functional groups on the complexes.

In this aspect of the invention, a peptide will contain: 1) helix-forming amino acids, 2) a repeating three-dimensional structure that contacts the major groove of the DNA, 3) suitable chromophores for quantitation, and 4) a number of "handles" (i.e., reactive sites) for regio-specific conjugation of ligands which form accessory functional domains. Examples of such peptides include NBC7 and NBC11. In these peptides, the threonine at position 1 is available for oxidation to glyoxal and therefore for conjugation via an oxime bond, tryptophan at positions 5 and 28 are chromophores which will allow quantitation in the presence and absence of DNA. The lysine at position 9 of NBC7 and the glutamic acid at position 9 of NBC11 are available for regio-specific conjugation via reductive amination, peptide bonds, etc., and the cysteine at position 16 for conjugation via thioether and disulfide bonds. The C-terminal glutamic acid of NBC7 is available for modification to a hydrazide and therefore for coupling via an oxime or hydrazone bond.

5) Another preferred nucleic acid condensing peptide is a peptide comprising a sequence which is derived from a sequence of histone H1 protein and other human histones.

Histone H1 is a highly basic protein of the histone family that is found in all higher organisms. Histone H1 unlike the majority of other members of this family does not assemble as an integral part of the nucleosome. Histone H1 is believed to interact primarily with those stretches of chromosomal DNA linking the nucleosome complexes of chromatin (Allen et al., (1980) Nature, 288). Histone H1 binds to naked DNA with the same salt dependence as H1 depleted chromatin (Kumar and Walker, (1980) Nucleic Acids Research, 8: 3135).

Histone H1 protein is not useful as a component of a gene therapy delivery vehicle because it is not readily available and is a biological repressor of its own transcription. Recombinant histone H1 cannot readily be produced by recombinant methods, and the protein is too large to be synthesized chemically. Purification of H1 from mammalian sources other than human cells poses a safety hazard. The use of histone H1 to promote the condensation of plasmid DNA for transfection is likely to reduce expression of the delivered gene because H1 is part of a general repressor mechanism where the presence of excess histone H1 leads to reduced transcription (Weintraub, H., (1985) Cell, 705–711; Croston et al., (1991) Science 251: 643).

Nucleic acid condensing peptides of the invention, however, may include those portions of H1 (sequence I, II or III, below) which are identified herein as sequences which possess the ability to condense nucleic acid. Therefore, a nucleic acid condensing peptide of the invention can comprise a linear combination of the following three consensus sequences where the total sequence length is >17 residues:
Sequence I:

-K-K-X-P-K-K-Y-Z-B-P-A-J-(SEQ ID NO:3)

where: K is Lysine, P is Proline; A is Alanine; X is Serine, Threonine or Proline; Y is Alanine, Proline, or Valine; Z is Alanine, Threonine, Lysine, or Proline; B is Lysine. Alanine, Threonine or Valine; and J is Alanine or Valine.
Sequence II:

-X-K-S-P-A-K-A-K-A-(SEQ ID NO:4)

where: X is Alanine or Valine; K is Lysine; S is Serine; P is Proline; and A is Alanine.
Sequence III:

-X-Y-V-K-P-K-A-A-K-Z-K-B-(SEQ ID NO:5)

where: X is Lysine or Arginine; Y is Alanine, Valine, or Threonine; Z is Proline, Alanine or Serine; B is Alanine, Lysine, Threonine or Valine; K is Lysine; P is Proline; A is Alanine.

Sequence IV is a consensus sequence from all human hi stone sequences:
Sequence IV:

-A-B-C-D-E-F-G-H-I-J-K-(SEQ ID NO:15)

where: A is preferably Lysine or Threonine; B is preferably Glycine or Glutamine; C is preferably Glycine, but can also be Aspartate, Glutamate, or Serine; D is preferably Glycine, but can also be Lysine, Valine, Glutamine, or Threonine; E is preferably Lysine or Alanine; F is preferably Alanine or Lysine, G is preferably Arginine, but can also be Valine or Isoleucine; H is preferably Alanine, but can also be Threonine, Histidine, or Proline; I is preferably Lysine, Arginine, or Glutamine; J is Alanine or Anginine; and K is preferably Lysine or Glutamine. A preferred consensus sequence is:

-K-G-G-G-K-A-R-A-K-A-K-(SEQ ID NO:16).

NBC1 has the following structure: $NH_2$-[SV40 NLS]-[Seq I]-[Seq II]-[Seq III]-[SV40 NLS]-[Seq I]-C-COOH (SEQ ID NO:6), where -C- is Cysteine;where the SV40 NLS has the sequence Pro-Lys-Lys-Lys-Arg-Lys-Val-Glu-(SEQ ID NO:25 (Dingwall and Laskey, (1991) Trends Biochem. Sci., 16: 478).

Therefore, another preferred nucleic acid condensing peptide of the invention will have an amino acid sequence that falls within the following generic sequence:

$NH_2$—X—(Y)$_n$—C—COOH, where X is either absent or Serine or Threonine; Y is sequence I (SEQ ID NO:8), II (SEQ ID NO:9), III (SEQ ID NO:10) or IV (SEQ ID NO:17) as defined above; n is 2–6; and C is Cysteine.

Particularly preferred peptides are the following:

NBC2 has the structure: $NH_2$-[Seq III]-[SV40 NLS1]-[Seq I]-C-COOH (SEQ ID NO:11). where -C- is Cysteine.

NBC8 has the structure: $NH_2$-[Con Seq I]-[Con Seq I]-C-COOH (SEQ ID NO:12) where -C- is Cysteine.

NBC13 has the structure: $NH_2$-[Seq I]-[Seq I]-[Seq I]-C-COOH (SEQ ID NO:13) where -C- is Cysteine.

NBC10 has the structure: $NH_2$-[Seq I]-[Seq I]-[Seq I]-[Seq I]-C-COOH (SEQ ID NO:14) where -C- is Cysteine.

Complexes prepared with NBC1 or NBC2 peptides are insoluble without salt at >20 µg/ml; therefore, these peptides are preferred where salt is present during complex formulation. Generally, if the complexes are conformationally pure and the peptide/DNA interactions stable, then this salt effect is not observed (charged particles tend to repel each other). However, it is preferred according to the invention, as described in detail hereinbelow, that some salt be present during formulation of a complex of the invention.

Sequences NBC8–10 are derived from part of NBC2, but lack the nuclear localization sequence and have a repeat motif (seq. I, II or III above) which has enabled us to look at the effect of peptide length on function. NBC8 has a double repeat of this sequence, NBC13 a triple repeat and in NBC 10 the sequence is quadrupled.

The sequences of NBC 1–2 and 4–14 are as follows.

NBC 1 NH2-PKKKRKVEKKSPKKAKKPAAKSPA KKAKAVKPK-AAKPKKPKKKRKVEKKS KKAKKPAAC(Acm)—COOH (SEQ ID NO:7)

NBC2 NH2-KPKAAKPKKPKKKRKVEKKSPKKA KKPAAC(Acm)-COOH (SEQ ID NO:11)

NBC4 NH2-KKAKSPAKAKAKAVKPKAAKPKKSPK KAKKPAYAC(Acm)-COOH (SEQ ID NO:18)

NBC5 NH2-KPKAAKPKKEVKRKKKPKKSPKK AKKPAAC(Acm)-COOH (SEQ ID NO:19)

NBC6 NH2-KAKAKAKPKAKAKAKPKAKAKA KPKAKAKAKPKAKAC(Acm)-COOH (SEQ ID NO:20)

NBC7 NH2-TRPAWRRAKRRAARRCGVSARRA ARRAWRRE-COOH (SEQ ID NO:1)

NBC8 NH2-KKSPKKAKKPAAKKSPKKAKKPAYC (Acm)-COOH (SEQ ID NO:12)

NBC9 NH2-TKKSPKKAKKPAAKKSPKKAKKP AAKKSPKKAKKPAAC(Acm)-COOH (SEQ ID NO:21)

NBC10 NH2-KKSPKKAKKPAAKKSPKKAKK PAAKKSPKKAKKPAAKKSPKKAKKPAYC(Acm)-COOH (SEQ ID NO:14)

NBC11 NH2-TKKAWKKAEKKAAKKCGVSAKKAA KKAWKKA-CONH2 (SEQ ID NO:2)

NBC12 NH2-TKKSPKKAKKPAAKKSPKKAK KPAAKKSPKKAKKPAYC(Acm)-COOH (SEQ ID NO:22)

NBC13 NH2-KKSPKKAKKPAAKKSPKKAKKPAA KKSPKKAKKPAYC(Acm)-COOH (SEQ ID NO:13)

NBC14 NH2-TKKKKKKKKKKKKKKKKKKC-COOH (SEQ ID NO:23)

The synthesis of NBC peptides are described in detail below. The synthesis of NBC conjugates, e.g., lipidated or insulin-derivatized NBCs are also described herein and according to chemical syntheses known to one of skill in the art.

Synthesis of NBC Peptides

Peptides NBC1–2 and 4–14 were synthesised using a Biosearch 9050 plus Pepsynthesizer in extended synthesis cycle mode using Fmoc-Cys(Acm)-O-PEG-PS-Resin with dimethylformamide as solvent. Deprotection of the N-terminal Fmoc-group before each coupling was achieved using a solution of 20% piperidine in dimethylformamide (1 min at a high flow rate followed by 10 mins at 3 ml/min). The amino acids were coupled in four fold excess using O-(1H-benzotriazo-1-yl)-tetramethyluronium tetrafluoroborate (TBTU)/1-hydroxybenzotriazole and N-ethyldiisopropylamine as activating agents. For NBC1 the coupling times started at 30 mins increasing by 15 mins after every 15th amino acid during the synthesis to 1.25 h. for the last 15 amino acids. For all the other NBC peptides, coupling times were set at 1 h throughout the synthesis. The following amino acid derivatives were used as appropriate for the NBC: Fmoc-Ala-OH, Fmoc-Arg(Pbf)-OH, Fmoc-Glu (OtBu)-OH, Fmoc-Lys(Boc)-OH, Fmoc-Pro-OH, Fmoc-Ser (tBu)-OH, Fmoc-Thr(tBu)-OH, Fmoc-Tyr(tBu)-OH, Fmoc-Val-OH. After the synthesis of each peptide was complete, the N-terminal Fmoc group was removed as described above to give the free amino, side chain protected, peptide bound to the resin. Each resin was then washed into a glass vial with methanol and dried in vacuo.

Peptides were cleaved from the resin using a TFA/water/phenol/thioanisole/1,2-ethanedithiol (82.5:5:5:5:2.5) mixture (10 ml of mixture for every gram of resin to be cleaved). The resin was then removed by filtration and washed 3 times with TFA. The combined filtrate and washings were concentrated by evaporation then precipitated using diethyl ether followed by centrifugation to give the crude peptide.

Crude peptides were dissolved in a small amount of 1% acetic acid in water and applied to a Sephadex G25 (superfine) (Pharmacia Biotech Inc., Piscataway, N.J.) gel filtration column of an appropriate size and eluted using the same 1% acetic acid solution. The fractions containing peptide, as determined by analytical reverse phase hplc, were pooled and lyophilised. Further purification was achieved by preparative reverse phase hplc using a Dynamax 83-221-C column and a gradient of 5–30% Acetonitrile(0.1% TFA) in Water(0.1% TFA) over 20 mins. The fractions containing peptide were pooled, the acetonitrile evaporated in vacuo, and lyophilised.

NBC1 was then desalted by dissolving it in 0.75 ml of 1% acetic acid in water and applying it to a PD-10 column which was then eluted using the same buffer. Fractions were taken every 0.75 ml and fractions 3–8 were combined and lyophilised to give the final peptide.

NBC2 and 4–14 were purified by preparative rp hplc, desalted by elution on a Sephadex G25 superfine column (1.6×30 cm) with 1% acetic acid in water. The resulting fractions were analysed by reverse phase hplc, pooled and lyophilised as above.

When necessary, the acetamidomethyl (Acm) thiol protecting group maybe removed using mercury (II) acetate in 30% acetic acid in water followed by precipitation of the mercury with 2-mercaptoethanol. The resulting free thiol peptide can be purified using gel filtration to give the desired product.

Lipid Derivatives of NBC Peptides

A conjugate may include a peptide which has a lipid group attached to it, and thus forms a lipid-derivatized nucleic acid condensing peptide. The term "lipid" is meant to refer to a four-thirty carbon molecule that is insoluble in water and soluble in alcohol. The term includes fats, fatty oils, essential oils, waxes, sterols, cholesterols, phospholipins, glycolipins, sulfolipins, aminolipins, chromolipins, and fatty acids. The nucleic acid condensing peptide can be specifically modified according to the invention by condensation with an lipid, for example, an activated ester of a fatty acid. The fatty acid is ideally either palmitic acid, oleic acid, such as dioleoylphosphatidylethanolamine, myristic acid, or cholesterol, although other fatty acids, such as stearic acid, may also be employed. Synthesis of NBC peptides conjugated to lipids are described in detail in the Examples. The effect of the presence of the lipid component on transfection efficiency of the complex is dramatic, leading to >40-fold increase in activity. The phenomenon is unrelated to the effect observed during DNA transfection using cationic lipids, where activity is proportional to the level of cationic lipid in the complex, in which the ligand density required for transfection is orders of magnitude higher (e.g., 10x–100x) than the ligand density required for gene transfer using complexes provided according to the present invention.

One advantage conferred by the presence of lipidated peptides in the complex or the complex formulation is resistance of the complex to degradation. The presence of lipidated peptide in the complex formulation confers higher resistance to inactivation by human plasma and increases the relative level of transfection after exposure of the complex to various levels of human plasma in the transfection medium.

Insulin Derivatives of NBC Peptides

Functionalization of Insulin

Insulin was chemically modified as described herein and according to previously described methods (pp.43–44 of Offord, R. E. (1980) "Semisynthetic Proteins", Wiley, Chichester and New York), with slight modifications. Briefly, 100 mg Zn-free insulin were dissolved in 1 ml of 1M sodium hydrogen carbonate, diluted with 4 mL dimethylformamide and reacted with an equimolar amount (relative to peptide amino groups) of methylsulphonyloxycarbonic acid N-hydroxysuccinimide ester. After 1 h incubation at room temperature, the mixture was acidified and subjected to semi-preparative HPLC on a C8 column equilibrated in 0.3M ammonium sulphate, pH 2.7, using a 65–90% gradient over 25 mins with a flow rate of 4 mL/min (A:0.3M ammonium sulphate, pH 2.7. B: 0.3M ammonium sulphate containing 35% acetonitrile. The ammonium sulphate solutions were obtained by dilution of a 3M stock solution which had been adjusted to pH 2.7 (glass electrode) with conc. sulphuric acid. No further adjustment was made to the pH of the diluted solutions. The peak corresponding to di-substituted insulin (as judged by subsequent electrospray mass spectrometry) was collected and desalted on a double Chromabond equilibrated in 0.1% TFA. The di-derivative obtained in such reactions is known to be preponderantly the desired A1, B29 substituted molecule. This supposition was checked as follows: analysis of the modified protein after overnight incubation in 50 mM dithiothreitol in water allowed validation that the B-chain contained only a single methylsulphonyloxycarbonyl group (calcd., m/z 3547.8; found m/z, 3549.6±0.4). 50 mg methylsulphonyloxycarbonyl2-insulin were then dissolved in 1 mL N-methyl-pyrrolidone and reacted with a 10-fold molar excess of Boc-AoA-OSu (synthesized according to Vilaseca et al., (1993) Bioconjugate Chem., 4: 515–520), in the presence of equimolar amounts of HOBT and sufficient N-ethylmorpholine to bring the pH, as indicated using moist pH paper, to approximately 8. After 1 h incubation at room temperature, the reaction medium was acidified and diluted with 0.1% TFA, and the derivatized insulin isolated by semi-preparative HPLC on a C8 column equilibrated in 0.1% TFA, using a 35–45% gradient (same eluants as described above) over 20 mins. The methylsulphonyloxycarbonyl groups were then cleaved under standard conditions and the material repurified on the C8 column using 35–40% gradient over 20 mins. The final compound, Boc-AoA-insulin, was characterized by electrospray mass spectrometry (calcd. m/z 5950.6; found m/z 5948.1±0.1) and was deprotected by TFA treatment (30 mins at room temperature) just before conjugation to a peptide, as described below.

Synthesis of NBC peptides conjugated to insulin are described in detail in the Examples.

Antibody/Peptide Conjugates

Cell targeting components such as monoclonal antibodies may be conjugated to a nucleic acid condensing peptide via the carbohydrate group or via a hydrazone and disulfide linkage or via a hydrazone and thioether linkage, or conjugation may provide a clustered antibody complex, all as described in detail below, to provide a complex for use in transfection according to the invention.

Clustered Glycosyl Conjugates

Glycosyl moieties may be clustered by the use of branched carbohydrates of natural or synthetic origin. Alternatively these groups may be clustered by modifying a branched amino acid backbone (dendrimer).

The glycosylated dendrimeric moieties described herein are based on a generic design of a ligand that, when conjugated to an NBC peptide, will give optimal binding of the peptide to either the hepatocyte asialoglycoprotein receptor (ASGPR) or the macrophage mannose receptor (MMR). The type of monosaccharide used in the synthesis of the ligand will depend on the receptor of interest. The design of the ligand is based on a consideration of the binding requirements of the ASGPR and the MMR, as it is these receptors that are of primary interest for use in gene targeting.

Ligands which present several (i.e three or more) monosaccharide units clustered together with their non-reducing ends exposed generally provide optimal binding to membrane lectins, including the ASGPR and MMR (Lee and Lee, (1987) Glycoconjugate J., 4: 317–328; Monsigny et al., (1994) Adv. Drug Del. Rev., 14: 1–24). Such ligands bind with more affinity than corresponding ligands presenting only one or two monosaccharide units—the so-called "cluster effect". Studies on the ASGPR have shown that the most successful ligands (in terms of binding affinity) are those which possess several monosaccharide moieties separated by an average distance of 1.5 nm. Theoretical calculations using "Hyperchem" modelling software shows that monosaccharide units such as those exemplified in the Man4Den2 (see below) structures are between 0.8 and 2.5 nm apart. In addition, Lee and Lee (1987) describe the optimal ligand for the ASGPR as having three galactose terminal residues with a triangular configuration, having intersite distances of 1.5, 2.2 and 2.5 nm. The binding requirements of the MMR have not been investigated as thoroughly as those for the ASGPR, although it is known that natural trisaccharides, which bind well to the MMR, present monosaccharides with intersite distances of between 1.0 and 3.0 nm.

Assembly of Complexes and Nucleic acid Condensation for Delivery to Cultured Cells (In Vitro)

The nucleic acid is made up to 20–400 µg/ml in the buffer. Peptide (or conjgate µg/µg+lipidated peptide µg/µg (µg/µg referring to µg peptide per µg DNA); DNA concentration; NaCl concentration. Buffer is normally 25 mM phosphate pH 7.4, but can be 25 mM Hepes pH 7.4. The amount of complex required for the experiment is calculated in terms of volume and total mass of DNA. The volumes of the different components required are calculated. The following stock solutions are used: NBC peptide or conjugate at 10 mg/ml or 1 mg/ml; Lipidated peptide at 10 mg/ml or 1 mg/ml; Phosphate buffer at 0.5M; NaCl at 5M; DNA—concentration is variable, normally 1–10 mg/ml. The total volume is made up with water.

Components are mixed in multiwell plates, or in microfuge tubes in the following order: NBC peptide, water, phosphate buffer, NaCl (components are mixed thoroughly after the addition of NaCl), DNA, lipidated peptide. After mixing, complexes are incubated at room temperature for 1 h, then stored at 4° C. Before the addition of transfection complexes to cells, they may be diluted into PEG diluent. If this is required, then 4 volumes of diluent are dispensed into a well of a multiwell plate. One volume of concentrated complex, at 100 µg/ml DNA concentration, is added so that the final DNA concentration is 20 µg/ml. PEG diluent=10% PEG 8000, 25 mM phosphate pH 7.4, 37.5 mM NaCl.

Characteristics of Nucleic Acid Condensing Peptide/Nucleic Acid Complexes of the Invention 1) Overall Charge Complexes of the invention will possess an overall (net) charge as follows. Complexes which are designed so as to target a particular cell type, and therefore contain a targeting ligand, will possess an overall charge in the range of 0.5–3.0, more particularly in the range of 0.5–2.0, and optimally in the range of 0.8–1.2. Particles which do not target a particular cell type, but are designed so as to transfect a broad range of cell types will possess an overall charge in the range of 0.5–5.0, more particularly in the range of 1.0–3.0, and optimally in the range of 1.3–3.0.

The overall charge (i.e., the balance of positive and negative charge species) of the complex are determined as follows. The number of moles of phosphate residues present in the nucleic acid component of the particle is estimated based on the amount of DNA to be used in the condensation reaction:

nM Phosphate in Condensation Reaction=(µg DNA/0.62)×2 (Assumes average molecular weight of one base pair=620.)

The number of moles of positively charged groups of each peptide is calculated based on the mass of the condensation peptides and conjugates to be added to the DNA:

nM Positively Charged Groups=(µg Peptide/Molecular Weight x 10-3) x No. of Positive Charges in Sequence.

The Charge Ratio is then:

=Σ(nM Positively Charged Groups)$_n$/nM Phosphate where n is each constituent peptide in the condensation reaction.

The nucleic acid condensing activity of peptides having different charges and the transfection efficiencies of complexes having different charge ratios are presented in Example 4. Transfection efficiencies of particles containing varying amounts of ratios of positively/negatively charged residues are presented in Example 7. Highly efficient transfection may be obtained using particles of the invention which do not contain a targeting ligand and are therefore untargeted with respect to a specific cell type. Such particles are highly efficient with respect to transfection where the ratio of positive/negative charges is greater than 1.25.

2) Overall Size

It is preferred according to the invention that the size of a virus like particle fall within the range of 5 nm to 500 nm. It has been found that the efficiency of uptake of the particle by a cell dramatically decreases when the particle size is greater than 500 nm. This is likely due to the size of the endosomal pores in a given cell type. Particle size is measured by lasar light scattering or atomic force microscopy, or electron microscopy. Therefore, the size of a particle of the invention will vary depending upon the cell type and the size of endosomal pores in a given cell type.

3) Ratio of nucleic acid condensing peptides/nucleic acid molecules.

A complex according to the invention will have a ratio of the number of peptide/the number of nucleic acid molecules in a particle that is within the range of 10/1 to 1,000,000/1. This ratio will depend upon the relative sizes of the peptide and nucleic acid molecules, the degree of condensing activity of the peptide, and the degree of condensation that the nucleic acid attains. More particularly, the range will be 100/1–10,000/1. For example, for NBC2 in combination with an 8 kb vector, a useful ratio for untargeted delivery of the vector to cells is approximately 5000:1 (relative numbers of molecules). For NBC14 conjugated to insulin in combination with an 8 kb vector, a useful ratio for targeted delivery of the vector to cells is approximately 1000:1. Where the nucleic acid is an oligonucleotide of, e.g., 10–50 nucleotides in length, the ratio of peptide/oligonucleotide is in the range of 0.1–10.0 and is preferably 0.5–1.0.

Transfection of Cells

Determining In Vivo Transfection Efficiency via Localized Administration

In order to demonstrate in vivo transfection efficiency, exogenous nucleic acid was transferred to mammalian cells in vivo. A representative in via cell transfection system is transfection of tumor cells using a murine carcinoma model.

The murine carcinoma model DBA2 containing the squamous epithelial syngenic tumour cell line KLN-205 was prepared as described in the Examples. A transfecting complex was prepared using a solution of plasmid DNA encoding a reporter gene or, for example, nitroreductase and a selected NBC peptide 0.5 µg peptide/µg DNA, as described herein. Where desired, a conjugate peptide was added to the transfecting complex, at a concentration of 0.1–0.3 µg 0.3 µg peptide/µg DNA.

Transfection efficiency may be determined in a number of ways, including assessing the effect of the reporter gene on the target tissue, or by quantitating the gene product. Below, tissues samples were obtained and nitroreductase gene expression was ascertained via staining of tissue sections.

Determining Ex Vivo Transfection Efficiency via Systemic Administration of Transfected Cells.

For ex vivo applications, cells are transfected ex vivo and reinjected into the animal. Reporter gene expression is then determined.

Determining In Vitro Transfection Efficiency

In vitro transfection efficiency is determined using plasmid DNA containing a marker gene for firefly luciferase (pRSVLuc; de Wet J. R., Wood K. V., DeLuca M., Helsinki D. R., and Subramani S., (1987) Mol. Cell. Biol., 7: 725–737). After incubation the cells are lysed and are assayed for gene expression. In the case of the luciferase reporter gene, luciferin and ATP are added to lysed cells and the light emitted is measured with a luminometer (see deWet et al., supra).

1. Assay for Transgene Expression Using Cells Grown in Suspension Culture.

Cell lines such as Jurkat and K562 grow in suspension and can be transfected and the level of transgene expression (luciferase activity) determined b) the following method. Cells are harvested on the day of assay by centrifugation at 1200 rpm for 5 mins at room temperature. The cell pellet is resuspended in phosphate buffered saline and re-centrifuged. This operation is performed twice. The cell pellet is then suspended in RPMI 1640 (Gibco Ltd.) to make up a suspension of $2.7 \times 10^6$ cells per ml. The cells are then aliquoted into tubes and 0.75 ml of RPMI medium added, followed by 0.04–0.08 ml of 100 mM Chloroquine and finally 0.25 ml of DNA-complex solution. The transfection is then allowed to proceed by incubating the cells at 37° C. for 4 h. After this time the cells are harvested by centrifugation at 2000 rpm. The cells are then suspended in 1 ml of RPMI medium and re-centrifuged. Finally the cells are suspended in 0.5 ml RPMI medium containing 10% foetal bovine serum. Each 0.5 ml of transfected cell suspension is transferred to a well of a 12 well plastic culture plate containing 1.5 ml of RPMI 10% FBS. The original transfection tube is rinsed with a further 1 ml of medium and the wash transferred to the culture dish making a final volume of 3 ml. The culture plate is then incubated at 37° C. for 24–90 h in an atmosphere of 5% CO2. The contents of each well in the culture dish are transferred to centrifuge tubes and the cells collected by centrifugation at 13000 rpm. The pellet is resuspended in 0.12 ml of Lysis Buffer (100 mM sodium phosphate, pH 7.8; 8 mM magnesium chloride, 1 mM EDTA; 1% Triton X-100 and 15% glycerol) and agitated with a pipette. The lysate is centrifuged at 13000 rpm for 1 min and the supernatant collected. 80 µl of the supernatant are transferred to a luminometer tube. The luciferase activity is then assayed using a Berthold Lumat L9501 luminometer. The assay buffer used is Lysis Buffer containing 10 mM Luciferin and 100 mM ATP. Light produced by the luciferase is integrated over 4s and is described as relative light units (RLU). The data are converted to RLU/ml of lysate, RLU/cell or RLU/mg protein (protein concentration of the lysate having been determined in this case by the BioRAD Lowry assay.

2. Assay for Transgene Expression Using Adherent Cells.

The method can be modified for adherent cells such as the hepatic carcinoma cell line HepG2. Cells were plated 24 h prior to transfection in 6-well tissue culture plates at a density of $1-2 \times 10^5$ per well in complete medium (MEM (with Earle's salts)+1% non-essential amino acids+10% foetal calf serum). Transfection was carried out by aspirating the culture medium and washing the cells with phosphate buffered saline. Complex (50 µg/ml DNA) is layered onto the cell monolayer in a 1 ml final volume containing 2.5 µg DNA and 120 µM chloroquine in RPMI supplemented with human albumin (1 mg/ml) and human transferrin (50 µg/ml). The transfection is then allowed to proceed by incubating the cells at 37° C. for 4 h, after which the transfection complex was removed, the cells washed with PBS and completed medium added prior to incubation at 37° C. for 24–72 h in an atmosphere of 5% CO2.

The cells were then harvested using trypsin to detach the cells. After addition of medium containing serum to inactivate the trypsin, cells were pelleted by centrifugation at 13,000 rpm. The cells were then suspended in 1 ml of PBS and re-centrifuged. The pellet was resuspended in 200 µl of Lysis Buffer (100 mM sodium phosphate, pH 7.8; 8mM MgCl2, 1 mM EDTA; 1% Triton X-100; 15% glycerol; 0.5 mM PMSF and 1 mM Dithiothreitol) and agitated with a pipette. The lysate is centrifuged at 13,000 rpm for 1 min and the supernatant collected. 80 µl of the supernatant are transferred to a luminometer tube. The luciferase activity is then assayed using a Berthold Lumat L9501 luminometer. The assay buffer used is Lysis buffer containing 0.01 mM Luciferin and 0.04375 mM ATP. Light produced by the luciferase is integrated over 4 sec and is described as relative light units (RLU). The data are converted to RLU/ml of lysate, RLU/cell or RLU/mg protein (protein concentration of the lysate having been determined in this case by the BioRAD Lowry assay.

Correlation of Biological Activity and nucleic acid KineticBinding and Dissociation Constants The relative transfection efficiencies observed in vivo can be correlated with the dissociation kinetics of peptide-nucleic acid bimolecular interactions measured using surface plasmon resonance (SPR). Condensation of nucleic acid with cationic peptides with an "off rate" apparent dissociation constant ($k_d$) of less than approximately $1 \times 10^{-5}$ sec$^{-1}$ or an equilibrium dissociation constant $K_D$ of less than approximately $1 \times 10^{-10}$ mol$^{-1}$ will lead to reduced transfection efficiency, presumably because condensed nucleic acid is unable to decondense within the cell.

When it is necessary to maintain high affinity for plasmid DNA (for example for transport of a gene into the nucleus using a conjugate peptide containing nuclear localization functional group), the conjugate should have a $k_d$ approaching (i.e., less than or equal to) approximately $1 \times 10^{-4}$ sec$^{-1}$, or a $K_D$ of less than $1 \times 10^{-9}$ mol$^{-1}$. Such peptides as NBC10 ($k_d$ of approximately $1 \times 10^{-3}$ sec$^{-1}$, $K_D$ of approximately $5.0 \times 10^{-9}$ mol$^{-1}$) and NBC11 ($k_d$ of approximately $1.6 \times 10^{-4}$ sec$^{-1}$, $K_D$ of approximately $7.8 \times 10^{-9}$ mol$^{-1}$ or $5 \times 10^{-10}$) have such binding characteristics but are not completely deleterious to transfection because dissociation is able to occur efficiently within the cell. This is not the case with polylysine (PolyK) which has an extremely high affinity for nucleic acid ($k_d$ of approximately $1 \times 10^{-6}$ and $K_D$ of approximately $5 \times 10^{-12}$) and extremely poor transfection efficiency.

For optimal transfection efficiencies, in ex vivo applications and in in vivo applications where it is important that decondensation does not occur as the complexes are diluted, the complex will comprise peptides or conjugates which which are substantially peptides or conjugate peptides having a $k_d$ in the range of approximately $1 \times 10^{-3}$ to $1 \times 10^{-4}$ sec$^{-1}$ or a $K_D$ in the range of approximately $1 \times 10^{-8}$ to $1 \times 10^{-10}$ mol$^{-1}$.

For in vivo applications where direct injection of the complexes occurs within a localized area, e.g., a tumour, optimal transfection efficiency is obtained using complexes which comprise peptides or conjugates which are substantially peptides or conjugates having a kd of approximately $1 \times 10^{-2}$ sec$^{-1}$ or $K_D$ of approximately $1 \times 10^{-6}$ mol$^{-1}$, such as in peptides NBC15 and NBC8.

For a chemically related series of peptides such as NBC15, NBC8, NBC9 and NBC10 the binding affinity required can be estimated from the following formula (FIG. 4):

$$K_D = 1 \times 10^{-4} \cdot e^{-0.4x}$$

where x is the number of cationic groups in the binding motif.

Thus, according to the invention, the transfection efficiency of a given complex in vivo or in vitro can be predicted from the $K_D$ and also from the number of cationic groups in the peptide from the correlation shown in FIG. 5.

In order that the invention described herein may be more fully understood, the following examples are set forth. It should be understood that these examples are for illustrative purposes and are not to be construed as limiting this invention in any manner.

EXAMPLES

The following examples describe the synthesis of nucleic acid condensing peptides used according to the invention (Example 1), the conjugation of functional groups to a condensing peptide, for example the conjugation of insulin to a nucleic acid condensing peptide, the conjugation of a lipid to a nucleic acid condensing peptide, the conjugation of a monoclonal antibody to a nucleic acid condensing peptide, and the conjugation of sugar groups to a nucleic acid condensing peptide (Examples 2–5); the determination of the affinity constant of a bimolecular interaction consisting of a nucleic acid condensing peptide and an immobilized nucleic acid using surface plasmon resonance according to the invention (Example 6); the assembly and formation of a nucleic acid condensing peptide/nucleic acid complex according to the invention (Example 7); and the testing of complexes for in vitro, ex vivo and in vivo transfection efficiency (Example 8–9).

Example 1

Synthesis of NBCs

Peptides NBC1–2 and 4–14 were synthesised using a Biosearch 9050 plus Pepsynthesizer in extended synthesis cycle mode using Fmoc-Cys(Acm)-O-PEG-PS-Resin with dimethylformamide as solvent. Deprotection of the N-terminal Fmoc-group before each coupling was achieved using a solution of 20% piperidine in dimethylformamide(1 min at a high flow rate followed by 10 min at 3 ml/min). The amino acids were coupled in four fold excess using O-(1H-benzotriazo-1-yl)-tetramethyluronium tetrafluoroborate (TBTU)/1-hydroxybenzotriazole and N-ethyldiisopropylamine as activating agents. For NBC1 the coupling times started at 30 mins increasing by 15 mins after every 15th amino acid during the synthesis to 1.25 h. for the last 15 amino acids. For all the other NBC-peptides, coupling times were set at 1 hour throughout the synthesis. The following amino acid derivatives were used as appropriate for the NBC: Fmoc-Ala-OH, Fmoc-Arg(Pbf)-OH, Fmoc-Glu(OtBu)-OH, Fmoc-Lys(Boc)-OH, Fmoc-Pro-OH, Fmoc-Ser(tBu)-OH, Fmoc-Thr(tBu)-OH, Fmoc-Tyr(tBu)-OH, Fmoc-Val-OH. After the synthesis of each peptide was complete, the N-terminal Fmoc group was removed as described above to give the free amino, side chain protected, peptide bound to the resin. Each resin was then washed into a glass vial with methanol and dried in vacuo.

Peptides were cleaved from the resin using a TFA/water/phenol/thioanisole/1,2-ethanedithiol (82.5:5:5:5:2.5) mixture (10 ml of mixture for every gram of resin to be cleaved). The resin was then removed by filtration and washed 3 times with TFA. The combined filtrate and washings were concentrated by evaporation then precipitated using diethyl ether followed by centrifugation to give the crude peptide.

Crude peptides were dissolved in a small amount of 1% acetic acid in water and applied to a Sephadex G25 (superfine) column of an appropriate size and eluted using the same 1% Acetic acid solution. The fractions containing peptide, as determined by analytical reverse phase hplc, were pooled and lyophilised. Further purification was achieved by preparative reverse phase hplc using a Dynamax 83-221-C column and a gradient of 5–30% Acetonitrile (0.1% TFA) in Water (0.1% TFA) over 20 mins. The fractions containing peptide were pooled, the acetonitrile evaporated in vacuo, and lyophilised.

NBC1 was then desalted by dissolving it in 0.75 ml of 1% acetic acid in water and applying it to a PD-10 column which was then eluted using the same buffer. Fractions were taken every 0.75 ml and fractions 3–8 were combined and lyophilised to give the final peptide.

NBC2 and 4–14 were purified by preparative rp hplc, desalted by elution on a Sephadex G25 superfine column (1.6×30 cm) with 1% acetic acid in water. The resulting fractions were analysed by reverse phase hplc, pooled and lyophilised as above.

When necessary, the acetamidomethyl (Acm) thiol protecting group maybe removed using mercury (II) acetate in 30% acetic acid in water followed by precipitation of the mercury with 2-mercaptoethanol. The resulting free thiol peptide can be purified using gel filtration to give the desired product.

Example 2
Synthesis of Ins Ia, Ins II, Ins-PEG-NBC14, Lip9

InsIa$^{B1}$-NBC14$^1$ (superscripts refer to linkage site on ligand and peptide) has the following structure:

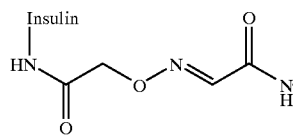—K—K—K—K—K—K—K—K—K—K—K—K—K—K—K—C—COOH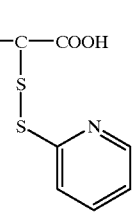

InsII$^{B1}$-NBC14$^1$ has the following structure:

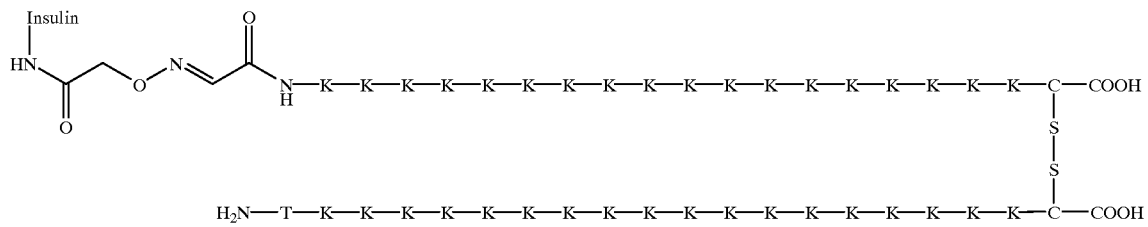

1. Conjugation of Insulin$^{B1}$-NBC14$^1$ Conjugate

Using functionalized insulin as described hereinabove, NBC14 was conjugated to functionalized insulin as follows.

The Cys-protected peptide was oxidized as follows. The peptide was dissolved in 50 mM imidazole (CI), pH 6.9 at a concentration of 10 mg/mL. and 0.2M methionine in water was added (as an anti-oxidant scavenger), a 10-fold molar excess over peptide. Then 50 mM sodium periodate was added to a five-fold molar excess over peptide, and the solution allowed to stand in the dark for 5 mins at room temperature, the mixture was purified by semi-preparative HPLC on a C8 column using a gradient of 10% to 60% solvent B over 25 min where solvent A is 0.1% (w/v) aqueous TFA and Solvent B is TFA/Acetonitrile-TFA-water 900:1:100 (V/W/V). The isolated oxidized peptide was dissolved into a solution of 5 mg of the AoA-insulin derivative (an approx 2-fold molar excess of peptide over insulin) made up in 0.5 ml, 0.1M sodium acetate buffer to which had been added 50 mL acetonitrile, followed by adjustment to pH 3.8 (glass elctrode) with glacial acetic acid.

The conjugate was isolated after 15 h incubation at room temperature and characterized by electrospray mass spectrometry (calculated. m/z 8426.1, found m/z 8429.3±0.5). 4 mg of material were isolated by semi-preparative HPLC with a 30–45% gradient from the bulk of the reaction mixture. The peak fraction was dried down in a SpeedVac vacuum centrifuge. The final yield was 4 mg of conjugate.

2. Construction of Insulin-PEG$_{3400}$ NBC9

N-α, A$^1$MSC, N-e,B$^{30}$-MSC-insulin (referred to as MSC)$_2$-Insulin) already used in the construction of AoA-Insulin is also an intermediate in the synthesis of insulin-PEG$_{3400}$-AoA.

40 mg (MSC)$_2$-Insulin were reacted with a 2-fold excess of Boc-NH-PEG$_{3400}$COOSu (from Shearwater Polymers, Huntsville, Ala., USA) in 500 μL N-methylpyrrolidone and the apparent pH brought to 8–9 with N-ethylmorpholine. The reaction medium was acidified after 2 h incubation at room temperature and the product isolated by preparative HPLC on the Waters C18 column (flow rate 20 mL/min using a 25–50%B2 gradient over 50 min as defined in the construction of the non-binding analogue of insulin, see below) The recovered material (43 mg) was then incubated 10 min in 2 mL TFA. After removal of the TFA under a N$_2$ stream, the material was dialysed against water to remove unreacted PEG which elutes with the modified protein on the HPLC column and finally lyophilised. The material can be characterized at this step by electrophoresis on cellulose acetate and migrates as a single spot with lower mobility than MSC)$_2$-insulin. The material was then reacted with a 2-fold excess Boc-AoA-OSu to introduce an aminooxy-acetyl group at the N-terminus of the PEG chain. Conditions of reaction and purification were the same as in the previous step. The isolated product (25 mg) was then deprotected by successive treatment with NaOH and TFA, as already described for the synthesis of AoA-Insulin and repurified by semi-preparative HPLC on a C8 column with a 30–50%B2 gradient over 40 mins. This derivative could be characterized by matrix-assisted laser desorption ionisation MS on a Voyager-Elite time of flight instrument (PerSeptive Biosystems). Laser desorption MS gave a bell-shaped spectrum centered at 9300 Da (theory 9250).

5.5 mg Insulin-PEG$_{3400}$-AoA was reacted with 4 mg of oxidised NBC9 dissolved in 600 uL 0.1M sodium acetate buffer containing 20%Ch$_3$CN, pH3.6 and the conjugate isolated after 15 h incubation, by semi-preparative HPLC on a C8 column with a 30–50%B2 gradient over 40 mins. The recovered material (4.5 mg) was characterized by Maldi-tof spectrometry (center of the bell-shaped curve, 113470 Da, for a calculated value of 13400) and by electrophoresis on cellulose as acetate.

3. Synthesis of a Conjugate Containing a Non-Receptor Binding Analogue of
Insulin (desB$^{23-31}$) InsulinB$^1$-NBC14$^1$ An insulin derivative which lacks the B$^{23-31}$ sequence (amino acids 23–31 from the amino terminus, "des-insulin") was prepared as follows: 70 mg of insulin were dissolved in 7.0 ml of 50 mM Hepes buffer, pH 8.0 and digested with 7 mg of TPCK-trypsin for 3 h at 37 C. The reaction was stopped by the addition of 140 ml of a 0.1M solution of p-methyl sulphonyl fluoride in ethanol and the addition of acetic acid until a pH 3.0 was attained. The des-insulin was isolated by preparative rp-hplc using a Waters Nova-Pak HR C18 column and an aqueous trifluoroacetic acid (0.1%) to acetonitrile/trifluoroacetic acid/water (900:1:100) gradient (20–40% gradient over 40 min). 38 mg of material were recovered and characterized by electrospray mass spectrometry (calculated mass 4865.5/observed mass 4867.7).

The introduction of an aminoxyacetyl group at the N-terminus of the B-chain of des-insulin was accomplished by an approach similar to that described by Offord (Offord, R. E. [1980], Semi-synthetic Proteins, p 235, Wiley, London and New York). 7.7 mM of des-insulin were dissolved in 0.5 ml of 1M sodium hydrogen carbonate and diluted with 1.75 ml of dimethyl formamide containing 9.4 mM of methylsulphonyloxycarbonate N-hydroxysuccinimide ester (Tesser [1975] Peptides, pp 53–56. John Wiley). After 1 h incubation at room temperature the mixture was acidified with trifluoroacetic acid and the derivative re-chromatographed under the same conditions described above. The peak corresponding to the mono-substituted derivative of des-insulin (as judged by electrospray mass specrometry (calculated mass 5015, observed mass 5018) was collected and freeze dried (25 mg recovered). This material was dissolved in 0.4 ml N-methyl-2-pyrollidone and reacted with a five fold molar excess of the N-hydroxysuccinimide ester derivative of Boc-aminooxyacetic acid [according to Vilasca et al [1993] Bioconjugate Chemistry 4, 515–520] in the presence of equimolar 1-Hydroxybenzotriazole (pH adjusted to 8.0 with N-ethylmorpholine). After incubation at room temperature for 1 h the reaction was acidified and the insulin derivative purified as described above. The methylsulphonyloxycarbonyl group was then cleaved under standard conditions and the peptide repurified by hplc as described above. 8 mg of aminooxyacetyl-des-insulin were recovered (calculated mass 4939/mass observed by electrospray mass spectrometry 4938).

Periodate oxidized NBC14 was prepared as described herein for NBC peptides. 4 mg of this material were mixed with 4 mg of des-insulin derivative in 400 ml of 0.1M sodium acetate buffer containing 20% acetonitrile, pH 3.6. After 15 h incubation at room temperature the conjugate was isolated by preparative hplc using a 1 cm diameter C8 column and a 30–35 % gradient of acetonitrile solvent (using Solvent A and Solvent B as described above). The recovered material (3.2 mg) was characterized by electrospray mass spectrometry (calculated mass 7465/observed mass 7462).

Example 3

Synthesis of Lipidated (N-Palmityl) NBC Derivatives

N-Palmitoyl derivatives of the corresponding NBC peptides are called Lip1, Lip2, etc. For example, the structure of Lip2 is: CH3-(CH2)14-CONH-KPKAAKPKKPKKKRKVEKKSPKKAKKPAAC(Acm) SEQ ID NO:11-COOH. An example of the synthesis of N-palmitoyl-NBC2 (Lip 2) is as follows. The synthesis of any lipidated peptide may be adapted accordingly.

Palmitic acid N-hydroxysuccinimide ester (0.5g per grain of resin) was added to a suspension of N-terminal amino deprotected resin bound NBC2 peptide (side chain protected)-O-PEG-PS resin in methanol/chloroform (1:4; 5 ml per gram of resin). The reaction was shaken for 48 h at room temperature then the resin was filtered off, washed 3 times with chloroform, washed with methanol and dried in vacuo.

The peptide was cleaved from the resin using a TFA/water/phenol/thioanisole/1,2-ethanedithiol (82.5:5:5:5:2.5) mixture (10 ml of mixture for every gram of resin to be cleaved). The resin was then removed by filtration and washed 3 times with anhydrous trifluoroacetic acid. The combined filtrate and washings were concentrated by evaporation then precipitated using diethyl ether followed by centrifugation to give the crude peptide.

The crude peptide was dissolved in a small amount of 25 mM HEPES pH 7.4 and applied to an SP-Sepharose fast flow column of an appropriate size and eluted using a gradient of 0–2M NaCl in 25 mM HEPES pH 7.4 over 20 column volumes. The fractions containing the peptide, as shown by analytical reverse phase hplc, were pooled and applied directly to a preparative reverse phase hplc (Dynamax 83-221 -C column) and eluted using an appropriate gradient of acetonitrile (0.1% TFA) in water (0.1% TFA) (typically 30–50% acetonitrile over 20 min). The fractions containing the desired peptide were pooled, the acetonitrile evaporated in vacuo and lyophilised. The LIP-peptides were desalted by elution on a Sephadex G25 superfine column (1.6×30 cm) with 1% acetic acid in water. The resulting fractions were analysed by reverse phase hplc and those containing pure peptide were pooled and lyophilised to give the final peptide.

Example 4

Conjugation of Monoclonal Antibody to NBC

1. Conjugation of Monoclonal Antibody to NBC1 via the Carbohydrate Group

The Carbohydrate groups present on the monoclonal antibody are oxidized using periodic acid to produce reactive aldehyde groups (Jentoft and Dearborn. (1979) J. Biol. Chem., 254: 4359). The oxidized antibody is then reacted with amino groups present on the NBC2 peptide. This results in the formation of an imine (Schiff Base) linkage between the antibody and the NBC polymer. The imine linkage is very labile in water and must be reduced using sodium cyanoborohydride or sodium borohydride to give the stable amine.

Anti-CD7 antibody (50 mg at 5 mg/ml) in 25 mM sodium acetate, pH 5.0 was oxidized by the addition of sodium periodate to 10 mM. The solution was left on ice, in the dark for 1 h. The oxidized antibody was desalted and the buffer exchanged to 25 mM MES, pH 6.0 on a Sephadex G25 column (30cm×2.5cm i.d.). The amount of antibody recovered from the column was determined by measuring the absorbance at 280 nm (the absorbance of a 1 mg/ml solution of antibody at 280 nm is 1.33). A 5 times molar excess of NBC1 was added and the solution was left at room temperature for 1 h. Sodium cyanoborohydride was added to 10 mM and the solution was left at room temperature for a further four hours, before dialyzing overnight against 0.6M sodium chloride; 25 mM HEPES, pH 7.9, in 12k moleclular weight cut off membranes. The conjugate was removed from dialysis and loaded onto a SP Sepharose column (5 ml) equilibrated in 0.6M sodium chloride; 25 mM HEPES pH 7.9. It was washed onto the column with 5 column volumes of the same buffer, then eluted with a gradient of 0.6M to 3.0M sodium chloride over 20 column volumes.

The unmodified antibody does not bind to the column and is washed through. The antibody conjugated to NBC1 binds to the column and is eluted early in the gradient. The conjugate peak eluted at approximately 1M NaCl.

2. Conjugation of Monoclonal Antibody to NBC2 via a Hydrazone and Disulfide Linkage To 20 mg anti-CD33 antibody in 25 ml 25 mM sodium acetate, pH 5.0, sodium periodate was added to a final concentration of 10 mM. After 3 h at room Temperature, the antibody was desalted by gel filtration using 25 mM sodium acetate, 0.5 M NaCl, pH 5.0, as running buffer. To the pooled protein fractions were added 5 mg (22 mnmol) 3-(2-pyridyldithio) propionyl hydrazide (PDPH) dissolved in 50 ml DMSO. After 1 h at room temperature the antibody-PDPH was purified by Sephadex G-25 gel filtration using 25 mM HEPES, 0.5M NaCl, pH 7.9, as running buffer. The protein fractions were pooled and stored at 4° C. NBC-2-SH (5 mg/ml) was reduced with dithiothreitol (dithiothreitol) and purified by gel filtration using 25 mM HEPES, 0.5M NaCl, pH 7.9, as running buffer. A total of 250 nmol NBC2 (as determined using an Ellman's test) were added to the antibody-PDPH and the solution was left for 16 h at room temperature. The concentration of NaCl was adjusted to 0.15M before the antibody-NBC2 conjugate was purified by cation exchange on SP Sepharose using NaCl gradient of 0.15–3M. The crude conjugate was applied to the column [S-Sepharose Fast Flow] (on 0.1 5M NaCl and eluted with a 0.15–3M linear gradient of NaCl. The conjugate peak eluted at approximately 1M NaCl. The protein peak was pooled and dialyzed against 0.02M HEPES buffer, 0.15M sodium chloride buffer, pH 7.2.

3. Conjugation of Monoclonal Antibodies to NBC2 via a Hydrazone and Thioether Linkage To 20 mg anti-CD33 antibody in 2.5 ml of 25 mM sodium acetate, pH 5.0, sodium periodate was added to a final concentration of 10 mM. After 3 h at room temperature in the dark, the antibody was desalted by gel filtration using 25 mM sodium acetate, 0.5M NaCl, pH 5.0, as running buffer. To the pooled protein fractions were added 5 mg (22 mmol) 3-(2-pyridyldithio)propionyl hydrazide (PDPH) dissolved in 50 ml DMSO. After 1 h at room temperature the reduced antibody-PDPH was purified by Sephadex G-25 gel filtration using 25 mM HEPES, 0.5M NaCl, pH 7.9, as running buffer. The protein fractions were pooled and stored at 4° C.

The derivatized antibody was reduced with cysteine and purified by gel filtration using 25 mM HEPES, 0.5M NaCl, pH 7.9, as running buffer. The fractions were pooled and the concentration of thiol groups determined using an Ellman FS test. A 2 molar excess of maleimido-b-Alanyl-NBC2-(S-acetamidomethyl-Cys) -COOH (5mg/ml) were added to the antibody-PDPH and the solution was left for 16 h at room temperature. The concentration of NaCl was adjusted to 0.1 5M before the antibody-NBC2 conjugate was purified by cation exchange on SP Sepharose using a NaCl gradient of 0.15–3M. The protein peak was pooled and the pool sterile filtered and the conjugate stored at 4° C.

4. Synthesis of a Clustered Monoclonal Antibody-NBC2 Conjugate Synthesis of Template Linker (2-bromoacetyl)-GG(E(NHNH2)GG)4.-NHNH2, (CL).

The peptide was synthesized using a Millipore 9050 plus peptide synthesizer equipped with enhanced counter-ion distribution monitoring to control the coupling time. Fmoc-Gly-O-Resin was used. After deprotection of the Fmoc group, using 20%, piperidine in dimethylformamide, the subsequent amino acids are coupled in four-fold excess using 0.6M N,N'-diisopropylcarbodiimide with 0.025% Quinoline Yellow in dimethylformamide and 0.6 M 1-hydroxybenzotriazole with 1 mM diisopropylethylamine in dimnethylformamide as activating agents. After the synthesis of the peptide was completed, the N-terminal Fmoc group was removed as described above and the peptide was cleaved from the resin using 95:5 TFA/water mixture. Purification of the peptide by gel filtration on Sephadex G25 followed by preparative reverse phase hplc gave the desired product.

The peptide may then be treated with 2-bromoacetic acid N-hydroxysuccinimidyl ester water to give the N-(2-bromoacetyl)-peptide. Followed by reaction of a solution of the peptide in water with a large excess of hydrazine in the presence of EDC-I to yield the N-(2-bromoacetyl)-penta-glutaryl-hydrazide derivative of the peptide.

5. Synthesis of a Clustered Monoclonal Antibody Ligand and its Conjugation to NBC2

To 20 mg anti-CD33 antibody in 2.5 ml 25 mM sodium acetate, pH 5.0, sodium periodate was added to a final concentration of 10 mM. After 3 h at room temperature in the dark, the antibody was desalted by gel filtration using 25 mM sodium acetate, 0.5M NaCl, pH 5.0, as running buffer. To the pooled protein fractions were added 5 mg of peptide. After 1 h at room temperature, the conjugate was purified by gel filtration and the peak pooled. A 2 molar excess of the thiol form of NBC2 was added to the clustered antibody derivative and the solution was left for 16 h at room temperature. The concentration of NaCl—was adjusted to 0.15M before the clustered antibody-NBC2 conjugate was purified by cation-exchange on SP Sepharose using a NaCl gradient of 0.15–3M. The protein peak was pooled and the pool sterile filtered and the conjugate stored at 4° C.

Example 5
Preparation of Sugar-conjugated Peptides

1. Modification of NBC1 using 4($\alpha$-D-mannopyranosyloxy)phenylisothiocyanate (Man1-NBC1)

4(a-D-mannopyranosyloxy)phenylisothiocyanate (MPIC) was synthesized from p-aminophenyl-a-D-mannose according to the method of Muller and Schuber ((1989) Biochem. Biophys. Acta, 986: 97–105).

10 mg (1.5 $\mu$mol) NBC1 were dissolved in 1.8 ml 25 mM HEPES, pH 7.9. To this solution was added 10 mg (32 $\mu$mol) of MPIC dissolved in 50 $\mu$l DMSO. DMSO was then added dropwise to the stirred solution to dissolve any remaining insoluble MPIC. The mixture was left at room temperature for 1 h before purification by gel filtration using 25 mM Hepes, 1.5 M NaCl, pH 7.9, as running buffer. The eluted fractions were analysed quantitatively for carbohydrate using the phenol-sulphuric acid method (Robyt, J. F. and White, B. J., (1987). *Biochemical Techniques: Theory and Practice*. Brooks/Cole, Calif.), and qualitatively for primary amine content using a ninhydrin test. The mannosylated NBC1 fractions were pooled and dialysed for 20 h against 25 mM HEPES, 0.15M NaCl, pH 7.5. It was estimated that 30% of the lysyl residues of NBC1 were mannosylated using this method.

2. Preparation of Mannosylated Lysine Dendrimer

The 2nd generation lysine dendrimer [Den2: (Lys)3-Gly-Gly-Tyr-Cys] SEQ ID NO:24 was synthesised using a Millipore 9050 Plus Pepsynthesiser running in extended cycle mode (1 h couplings) with TBTU/N-ethyldiisopropylamine activation and deprotection with 20% Piperidine in dimethylformamide. Starting from Fmoc-Cys (Trt)-O-PEG-PS resin, and with a four-old excess of activated amino acid to free amine group, the peptide was synthesised sequentially using the following amino acid derivatives; Fmoc-O(tert-butyl)-tyrosine; Fmoc-glycine, di-Fmoc-lysine and Fmoc-Ne-tert-butoxycarbonyl lysine. After the final coupling had finished the N-terminal Fmoc groups were removed using 20% piperidine in dimethylformamide.

The peptide was cleaved from the dried resin using reagent K (TFA, water, phenol,thioanisole,1,2-ethanedithiol; 82.5:5:5:5:2.5) and purified by ion-exchange (SP-sepharose) and reverse phase hplc.

To 15 mg (20 mmol) of the dendrimer in 1 ml of a 1:1 acetonitrile: water mixture, 6 mg (1.5 molar equivalents) of 2,2'-dipyridyldisulphide in 100 ml ethanol were added. After leaving the mixture for 5 mins at room temperature, the peptide was purified by hplc.

10 mg (12 mmol) lyophilised peptide were dissolved in 1 ml of 1:1 acetonitrile: 0.1M borate, pH 9.0. The pH was adjusted to 9.0 by addition of NaOH. The peptide solution was then added to 95mg 4-(a-D-mannopyranosyloxy)-phenylisothiocyanate dissolved in 1 ml of the acetonitrile/borate solution. The mannosylation was left to proceed at 37° C. for 16 h.

The thiol of the mannosylated peptide was reduced by adding 20 mg solid dithiothreitol. The peptide was then purified by high resolution gel filtration.

By using appropriate spectrophotometric assays, the mannosylated peptide was determined to possess, on average, between 3 and 4 mannose groups per peptide molecule.

3. Conjugation of Mannosylated Dendrimer Ligand Man4Den2 to NBC12 (Synthesis of Conjugate Man4DEN2-NBC12l)

41.2 mg (10.2 mmol) NBC12 in 1.0 ml 50 mM imidazole, pH 6.9, were oxidised by the addition of 0.50 ml 0.1M sodium periodate prepared in the imidazole buffer. After 5 min reaction at room temperature the reaction was stopped by the addition of 0.50 ml ethylene glycol (commercial solution). The medium was acidified pH 3.0 using acetic acid before purification by reverse phase HPLC. After lyophilization 30.0 mg oxidised NBC12 was obtained.

A maleimide function was introduced into NBC12 by addition of 4.3 mg (12.2 mmol) 4(-4-maleimidophenyl) butyric acid hydrazide. HCl. ½ dioxane to 10 mg (2.5 mmol) oxidised NBC12 in 2.0 ml 0.1M sodium acetate, pH 4.6, containing 20% acetonitrile. After 15 h incubation at room temperature the hydrazone was purified by gel filtration in 1% acetic acid, pH 4.7. The peptide solution was lyophilised.

1.0 ml 50% acetonitrile/water containing 3.2 mmol of peptide (as determined by thiol analysis) was added to 5.0 mg (1.1 mmol) MAL-NBC12 in 0.1 M HEPES, pH 7.5 containing 20% acetonitrile. After 2 h incubation at room temperature the material was purified by reverse phase preparative HPLC and immediately lyophilised. The peptide construct was named Man4Den2-NBC12l.

4. Preparation of Mannosylated Lysine Dendrimer—NBC12 Coniugate Man4DEN5-NBC12l

Man4Den5-NBC12 is a mannosylated dendrimer derivative of NBC-12, similar in structure of Man4Den2-NBC 12l. In this case however the mannosyl side chains are introduced using solid phase peptide synthesis coupling methods with the tetra-o-acetyl-mannose-a-Fmoc-Serine derivative.

The peptide dendrimers were synthesised using a Millipore 9050 Plus Pepsynthesizer as described above except that Fmoc-Ne-tert-butoxycarbonyl lysine was replaced by di-Fmoc-lysine.

With the peptides on the resin, the four Fmoc-protected amine groups were deprotected using 20% piperidine in dimethylformamide. The free amines were then reacted with a tetra-O-Ac-mann-a-Fmoc-serine residue (in 16-fold molar excess of peptide) with TBTU/N-ethyldiisopropylamine as activating agent. After the coupling had finished, N-terminal Fmoc groups were removed using 2% DBU in dimethylformamide containing 2% piperidine.

The glycopeptides were cleaved from the resin by adding an excess of 95% TFA for 2 h at room temperature. The glycopeptide was precipitated in 10 volumes of ether, the ether discarded after centrifugation and purified by hplc.

In order to remove the O-acetyl protecting groups present on the carbohydrate moiety, the peptides were treated with NaOMe/MeOH before a final purification by HPLC.

The glycopeptide, Man4Den5 was coupled to NBC12 via a maleimide-hydrazide bifunctional crosslinker, as described above. Alternatively the glycopeptide was synthesised with a C-terminal hydrazide group by using a hydroxymethylbenzoic acid (HMBA) resin linker and cleavage method, as described in "synthesis of Man4Den4". Such hydrazide derivatives can be used to couple the Man peptide directly to oxidised NBC12, as described for the synthesis of Man4Den4-NBC 12.

5. Biological Activity of Mannosylated NBC1

In order to assess the potency of Man1—NBC1, transfer of the luciferase gene to HepG2 cells in culture was measured. The assay was carried out as described herein for in vitro transfection assays except the chloroquine concentration was increased from the standard 120 mM to 240 mM and the HepG2 cells were cultured for both 24 h and 90 h prior to enzyme assay.

Example 6

Measurement of Binding Kinetics by Surface Plasmon Resonance

1. Preparation of Biotinylated Plasmid DNA

A 6 kilobase (kb) plasmid DNA (pRSVLuc) was biotinylated using photoactivatable biotin (Pierce and Warriner) as per manufacturer's instructions. Estimated biotin level is one biotin every 100–400 bases.

2. Preparation of Sensor Chip

A sensor chip with immobilized streptavidin (SA5) was conditioned following manufacturer's instructions, i.e., three one-minute injections of 1 M NaCl: 50 mM NaOH followed by one 1 min injection of 0.5% SDS. Flow rate on the BIAcore sensing device was 20 µl per min, running buffer was phosphate buffered saline (PBS). Flow path was flow cells 1 and 2.

The flow path was switched to flow cell 2 only and the flow rate was reduced to 10 µl per minute. Biotinylated plasmid at a concentration of 200 µl/ml in 0.5M NaCl was injected for 3 mins. This resulted in an increase of 614 RU after the injection.

3. Analysis of Peptide-Nucleic acid Interactions

Phosphate buffered saline was used as running buffer at a flow rate of 20 µl per minute. The flow path was over flow cells 1 and 2. Flow cell 1 was used as a reference cell. The experiments were carried out at a temperature of 25° C.

Peptides were injected at various concentrations for three minutes. The injection was followed by a 5 min dissociation phase before the injection port was washed. The sensor chip was regenerated by the injection of 2M NaCl for 1 min. If necessary, this injection was repeated to bring the response back down to baseline before the next peptide sample was injected.

4. Calculation of Kinetic Constants

The data was analysed using the methods described in the handbook (BIAevaluation 2.1. Software Handbook, Pharmacia Biosensor AB, Uppsala, Sweden).

Essentially the plots were evaluated as follows: The dissociation constant, $k_d$, was determined first. A curve or family of curves (same NBC at different concentrations) were plotted as response (Y) versus time as Ln (Yo/Y) versus time. In the area where the Ln(Yo/Y) curve was linear, a fit of the default dissociation model [AB]=[A]+[B] was made. The association constant, $k_a$, was then calculated by fitting the related association model on that part of the association curve where a plot of ln(abs(dY/dt) versus time was linear. $K_D$ were approximated by dividing the calculated $k_d$ with the calculated $k_a$.

Example 7
Preparation of Complexes for In Vivo Delivery

Formulations are referred to in the following manner:

Peptide (or conjgate μg/μg+lipidated peptide μg/μg (μg/μg referring to μg peptide per μg DNA); DNA concentration; NaCl concentration. Buffer is normally 25 mM phosphate pH 7.4, but can be 25 mM Hepes pH 7.4. The amount of complex required for the experiment is calculated in terms of volume and total mass of DNA. The volumes of the different components required are calculated. The following stock solutions are used: NBC peptide or conjugate at 10 mg/ml or 1 mg/ml; Lipidated peptide at 10 mg/ml or 1 mg/ml; Phosphate buffer at 0.5M; NaCl at 5M; DNA—concentration is variable, normally 1–10 mg/ml. The total volume is made up with water.

Components are mixed in multiwell plates, or in microfuge tubes in the following order: NBC peptide, water, phosphate buffer, NaCl (components are mixed thoroughly after the addition of NaCl), DNA, lipidated peptide. After mixing, complexes are incubated at room temperature for 1 h, then stored at 4° C. Before the addition of transfection complexes to cells, they may be diluted into PEG diluent. If this is required, then 4 volumes of diluent are dispensed into a well of a multiwell plate. One volume of concentrated complex, at 100 μg/ml DNA concentration, is added so that the final DNA concentration is 20 μg/ml. PEG diluent=10% PEG 8000, 25 mM phosphate pH 7.4, 37.5 mM NaCl.

Example 8
In Vivo and Ex Vivo Transfection of Tumor Cells Using Peptide-Nucleic Acid Complexes
Localized Administration of Complexes The ability to transfect tumor cells in vivo in mice was tested using plasmid nucleic acid carrying the nitroreductase reporter gene condensed on each of the following peptides: NBC15, NBC8, NBC9, NBC11, NBC7.

The experiment was performed as follows.

1. Injection of Tumor Cell Line for the Formation of Tumors in DBA2 Mice

DBA2—male mice, aged 5–10 weeks were injected subcutaneously in each flank with a squamous epithelial syngenic tumour cell line KLN-205. The cell line was grown up in 175 ml T-flasks in standard EMEM medium containing 10% foetal calf serum. When the cells reached a density of $4 \times 10^6$ they were suspended by a standard trypsinization technique, washed in PBS and diluted to a final concentration of $5 \times 10^{-9}$ cells/50 μl.

The mice were anaesthetized before injection using the following preparation: The anaesthetic used is Enflurane (Alynane; Anaquest, Ltd., Windlesham, Surrey, UK); Ketamine (10% Ketaset, Willows Francis Veterinary, Cramley, West Sussex, UK); Rompun (2%, Bayer UK, Ltd., Suffolk, UK). For 10 ml anaesthetic mixture: 8.6 ml PBS, 1 ml Ketamine. 0.5 ml Rompun. Each animal was injected intra-peritoneally with 200 μl/animal using 1 ml syringe with 25 gauge needle. When anaesthetized, the mice were injected with the cell suspension as follows: 2 cm² areas on both flanks of the animal were shaved and 50 μl of the cell suspension injected subcutaneously into each flank using a 1 ml syringe with a 25 gauge needle. The mice were then kept until the tumours were palpable.

Once tumours appear palpable, growth was monitored on a daily basis and sized documented via their longest dimension. Once tumours reach desired size (5–8-mm is acceptable) then can be injected.

2. Administration of Peptide/Nucleic Acid Complex.

The mice were first anaesthetized as follows:

The anaesthetic was Enflurane (Alynane; Anaquest, Ltd., Windlesham, Surrey UK): Ketamine (10% Ketaset, Willows Francis Veterinary, Cramley, West Sussex, UK); Rompun (2%, Bayer UK, Ltd., Suffolk, UK). For 10 ml anaesthetic mixture: 8.5 ml PBS; 1 ml Ketamine; 0.5 ml Rompun. Each animal was injected intra-peritoneally with 200 μl/animal using 1 ml syringe with 25 gauge needle. Once anaesthetized, the tumour is manipulated between the fingers lifting it slightly away from the animal's body and at the same time apply minimum pressure to the tumour. Using a 0.5 ml insulin needle the formulated delivery vehicle (a plasmid containing the E. coli nitroreductase gene condensed on a peptide at a ratio of 0.5 μg peptide/μg DNA) to be injected is taken up and the tumour is injected horizontally trying to avoid any visible blood vessels and necrotic or abnormal tissue. Daily monitoring is continued until the experiment is terminated.

3. Assay for Transgene Expression (Nitroreductase) in Tumor Cells via Immunostaining of Cryostat Sections 7μ sections of frozen tumour tissue are prepared using standard methods and a Cryostat and air dried. Sections are fixed with freshly prepared 4% PFA/PBS for 30 mins at room temperature and then washed twice with 0.01% Tween-20/PBS 5 mins each wash. Sections are then immersed in 0.25% hydrogen peroxide/PBS, at room temperature (20C.) for 30 mins, and then washed three times in 0.01% Tween 20/PBS for 5 mins each wash. Sections are then permeabilised by treatment with ice cold 0.1 % TRITON X-100 for 5 mins, followed by a further two washes in 0.01% Tween-20/PBS 5mins each wash. The sections are then blocked with 5% NGS/PBS 60mins at room temperature in a wetbox. After decanting the blocking solution, 0.5 ml diluted antiserum/slide (1:400 in 2.5% NGS) is added and the sections incubated for 60 mins at room temperature. Slides are then washed three times in 0.01% Tween-20/PBS 5 mins each wash. Secondary antibody (0.5 ml) from ABC Elite Vector stain kit is added as follows and incubated 30 mins at room temperature in a wetbox.

The antibody solution was as follows: PBS (10 mls), NGS (0.15 ml), antibody (0.05 ml). The staining solution was prepared 30 mins prior to use, and included: 5 mls PBS, 2 drops solution A, 2 drops solution B.

Sections are washed three times in 0.01 % Tween-20/PBS 5 mins each wash followed by addition of 0.5 ml Vector stain per slide and incubated 30 mins room temperature in a wetbox. The slides are then washed three times in PBS, 5 mins each wash.

0.5 ml AEC substrate (from Vector AEC Kit, Vector Labs) was added per slide freshly prepared as follows and incubate for 5 mins at room temperature. (5 mls glass distilled water; 2 drops stock buffer and mix; 3 drops AEC and mix; 2 drops hydrogen peroxide and mix.)

The reaction was stopped in tap water, 5 mins, and the sections mounted in mowiol?? (stored in the dark to help prevent fading).

Systemic Administration

Ex vivo transfection efficiency was determined by transfecting tumor cells ex vivo injecting the transfected cells IP into the animal, and determining transfection efficiency, as follows.

1. Injection of Cell Lines for the Formation of Tumors in Mice

Mice were DBA2 —Male, age 5–10 weeks. Culture of the adherent cell line KLN-205 (ATCC) were grown in 10% FCS in EMEM+1% NEAA (Life Fechnologies, Gaithersburg, Md.) and subcultured using a standard trypsin- EDTA treatment prior to transfer. The approximate number of cells from T175 is $4 \times 10^6$. Two subculture steps were performed.

2. Cell Preparation

Following trypsinisation, the cells were washed three times in PBS. The final concentration of cells was $1 \times 10^6/100$ $\mu l$ (animal), i.e. $5 \times 10^5/50$ $\mu l$–50 $\mu l$ injected/flank. Mice were anaesthetized with Enflurane (Alynane; Anaquest, Ltd., Windlesham, Surrey, UK); Ketamine (10% Ketaset, Willows Francis Veterinary, Cramley, West Sussex. UK); and Rompun (2%, Bayer UK, Ltd., Suffolk, UK). For each 10 ml anaesthetic mixture: 8.5 ml was physiological saline; 1 ml Ketamine; and 0.5 ml Rompun.

Animals were anaesthetized by injectiing 200 $\mu l$/animal interperitoneally using 1 ml syringe with 25G needle. Animals were fully anaesthetized in approximately 5 mins.

3. Procedure

Approximately 2cm$^2$ area on both flanks of the animal were shaved and inject 50 $\mu l$ of the cell suspension sc into each flank using a 1 ml syringe with a 25G needle. The cell suspension was thoroughly mixed prior to each injection and also between animals which resulted in similar growth on both sides of all animals.

A standard ELISA was performed using Amersham antisera. That is, the antigen solution was prepared in coating buffer. The amount should be determined by chequer-board, however in the range of 50 mg/100 $\mu l$ coating buffer is a typical amount to use. Using a flat bottomed 96 well ELISA plate, wells are filled with 100 $\mu l$ of antigen/coating buffer. The plate is sealed with parafilm to avoid evaporation. The plate is incubated overnight at 4° C. or 37° C. 2 h. A wash is then performed with PBS/Tween. 1001 $\mu l$ of primary antibody is applied to a first column of wells, and the remainder of wells are double diluted across the plate, leave the last column as negative control i.e. PBS/Tween. The plate is then incubated.

Figure 6A:
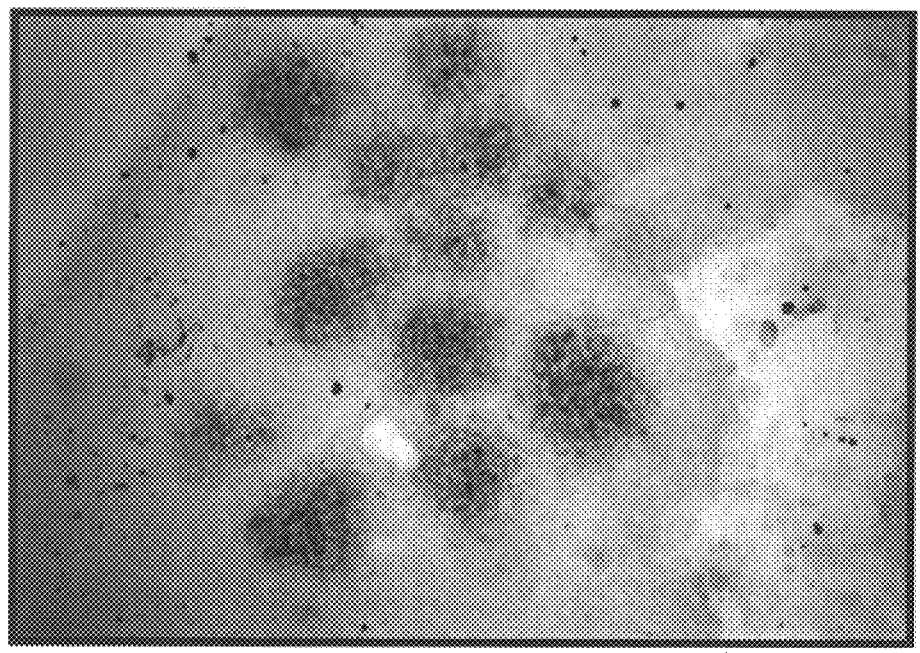
FIGS. 6A and 6B show results of immunostaining of tumor cells using nucleic acid condensing peptide/nucleic acid complexes according to the invention.
Figure 6B:
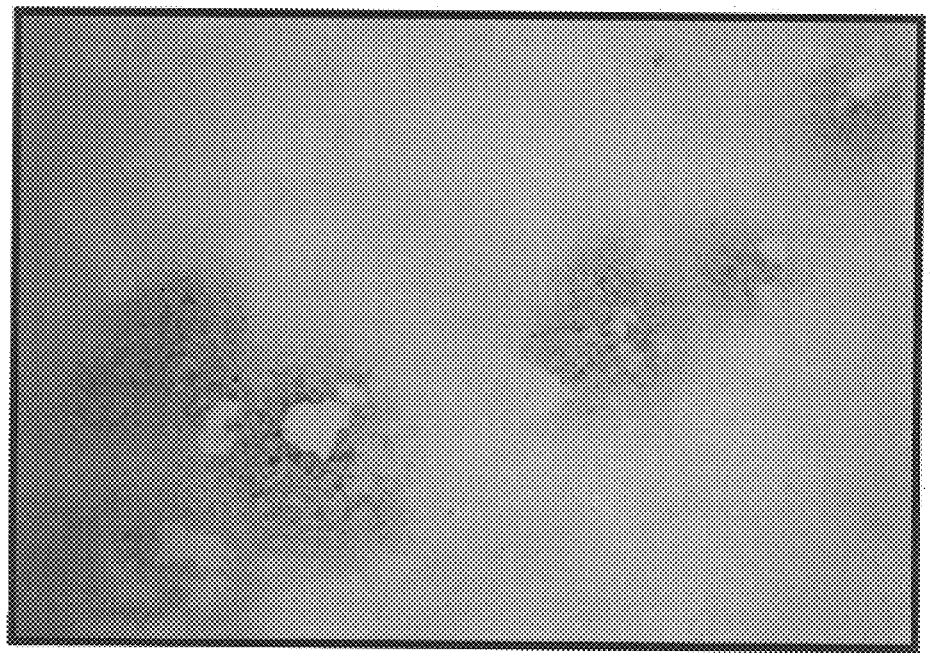

FIG. 6 shows the frequency of transfection of tumor tissue cells obtained with complexes of NBC15 and NBC9 were used. Of the group of peptides tested as peptide components in a gene delivery system, the highest number of transfected tumor cells was obtained using peptide-nucleic acid complexes containing the NBC15 peptide (i.e., most efficient transfection) and the fewest number of transfected tumor cells was obtained using complexes containing a poly-lysine peptide (i.e., least efficient transfection). FIG. 6(a) shows the transfection pattern obtained when tumours are injected with plasmid pTX 118 formulated with 0.5 $\mu g$ NBC15 peptide/$\mu g$ DNA. The tumour is a murine syngenic squamous carcinoma produced by subcutaneous injection of KLN205 cells. When the tumours were approximately 4 mm in diameter they were injected with 20 $\mu l$ of plasmid DNA formulated with the NBC15 peptide. After 48 h the tumours were excised and sectioned by standard histological techniques and immunostained for expression of the transgene (*E. coli* nitroreductase). The figure shows large numbers of cells in the tumour expressing the transgene (stained red). FIG. 6(b) shows a similar experiment. In this case the tumours were injected with the same plasmid formulated in 0.5 $\mu g$ NBC9 peptide/$\mu g$ DNA. Although transfection is evident the level of transfection is noticeably lower. The relative ability of the peptides in this study to transfect cells can be summarized in a ranking based on the numbers of transfected tumor cells obtained as an indication of transfection efficiency, i.e., from most efficient transfection to the least efficient transfection: NBC15>NBC8, NBC9, NBC11>NBC7>>>poly-lysine.

Incorporation of lipidated peptides into complexes quantitatively reduced transfection efficiency, suggesting that the high affinity of a lipidated peptide for nucleic acid resulted in failure of the condensed nucleic acid to decondense in the cell.

Example 9

In Vitro Transfection of Tumor Cells Using Peptide-Nucleic acid Complexes

In order to compare the relative efficiency of transfection of complexes composed of different NBC condensation peptides or poly-L-lysine, pRSVLuc DNA at a concentration of 100 $\mu g$/ml was condensed using peptide at a ratio of 2 $\mu g$/$\mu g$ plasmid DNA as described herein with the following deviation: prior to addition to the cells (Jurkat cell line) the complexes were diluted to 20 $\mu g$/ml with 10% PEG 10 000; 37 mM sodium chloride; 25 mM sodium phosphate, pH 7.4. The cells were assayed for luciferase after 24 h. The relative transfection efficiency of individual NBC peptides and a polylysine peptide is shown in FIG. 7.

FIG. 7 of describes transfection of a cell line with a luciferase plasmid condensed with different cationic peptides and shows a rank in order of relative transfection efficiency of: (most efficient) NBC11>NBC13>NBC8>>NBC15>>>polylysine (least efficient).

The results show that all the peptides of low polydispersity including NBC 14 (a synthetic poly-L-lysine having low polydispersity) were significantly better transfection agents than the polydisperse poly-L-lysine.

The results also show that incorporation of lipidated peptides in such in vitro experiments can lead to increased transfection efficiencies. However, complete condensation of nucleic acid with palmitoyl—NBC2 (Lip2) alone, led to extremely poor transfection efficiencies. On the other hand, in the presence of free underivatized peptide, transfection efficiency is augmented (FIG. 8). FIG. 8 shows that an optimal ratio of Lip2 to NBC2 can boost transfection by more than two orders of magnitude. For the data provided in FIG. 8, complexes were assembled as described herein using NBC2 and Lip2 as condensing peptides. When the nature of the lipidated peptide was varied in complexes made up of 0.6 $\mu g$ lipidated peptide/2 $\mu g$ free NBC9 peptide per $\mu g$ DNA (FIG. 9), the following order of transfection activity was observed: Lip8>Lip9>Lip7. Because NBC9 and NBC 13 differ only at the penultimate carboxy terminal amino acid, one would expect that NBC 13 and Lip 13 would have similar transfection activities as NBC9 and LIP9, respectively.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of screening test peptides for the ability to optimally transfect cells with a nucleic acid molecule comprising:
   detecting a change in the surface plasmon resonance of a nucleic acid immobilized on a sensor chip and exposed to a solution of a test peptide, wherein said change in surface plasmon resonance occurs upon binding of the peptide to and dissociation of the peptide from the immobilized nucleic acid, thereby to permit calculation of the equilibrium constant $K_D$ (or apparent dissociation constant, $k_d$); and
   selecting the peptide having an equilibrium rate constant, $K_D$, with a value of approximately $1\times10^{-12}$ to $1\times10^{-6}$ (or apparent dissociation constant, $k_d$, with a value of approximately $1\times10^{-6}$ to $1\times10^{-1}$).

2. A method of screening test peptides for the ability to optimally transfect cells with a nucleic acid molecule comprising:
   detecting a change in the surface plasmon resonance of a nucleic acid immobilized on a sensor chip and exposed to (a) a solution containing a test peptide for a time sufficient to permit binding of the peptide to the immobilized nucleic acid followed by (b) a solution lacking test peptide for a time sufficient to permit dissociation of the peptide from the immobilized nucleic acid, wherein said change in surface plasmon resonance occurs upon binding of the peptide to and dissociation of the peptide from the immobilized nucleic acid, thereby to permit calculation of the equilibrium constant $K_D$; and
   selecting a peptide having an equilibrium rate constant, $K_D$, with a value of approximately $1\times12^{-12}$ to $1\times10^{-6}$.

3. A method of screening test peptides for the ability to optimally transfect cells with a nucleic acid molecule comprising:
   detecting a change in the surface plasmon resonance of a nucleic acid immobilized on a sensor chip and exposed to (a) a solution containing a test peptide for a time sufficient to permit binding of the peptide to the immobilized nucleic acid followed by (b) a solution lacking test peptide for a time sufficient to permit dissociation of the peptide from the immobilized nucleic acid, wherein said detection detects a change in surface plasmon resonance which occurs upon dissociation of the peptide from the immobilized nucleic acid, thereby to permit calculation of the apparent dissociation constant, $k_d$; and
   selecting a peptide having an apparent dissociation constant, $k_d$, with a value of approximately $1\times10^{-6}$ to $1\times10^{-1}$.

4. The method of any one of claims 1–3, further comprising, prior to the detecting step, the steps of
   immobilizing the nucleic acid on a sensor chip; and
   exposing the immobilized nucleic acid molecule to a solution of a test peptide.

5. The method of claim 4, further comprising the step of recording said change in surface plasmon resonance.

6. A method of screening test peptides for the ability to optimally transfect cells with a nucleic acid molecule comprising:

immobilizing the nucleic acid on a sensor chip;

exposing the immobilized nucleic acid molecule to a solution of a test peptide;

detecting and recording a change in the surface plasmon resonance upon binding of the peptide to the immobilized nucleic acid;

calculating the equilibrium constant $K_D$ (or apparent dissociation constant, $k_d$) of the test peptide from the recorded change in surface plasmon resonance; and selecting the peptide having an equilibrium rate constant, $K_D$, with a value of approximately $1\times10^{-12}$ to $1\times10^{-6}$ (or apparent dissociation constant, $k_d$, with a value of approximately $1\times10^{-6}$ to $1\times10^{-1}$).

7. The method of any one of claims 1, 2 and 4–6, wherein the peptide selected has an equilibrium rate constant, $K_D$, with a value of approximately $1\times10^{-12}$ to $1\times10^{-6}$.

8. The method of claim 7, wherein the peptide selected has an equilibrium rate constant, $K_D$, with a value of approximately $1\times10^{-6}$.

9. The method of any one of claims 1, and 3–6, wherein the peptide selected has an apparent dissociation constant, $k_d$, with a value of approximately $1\times10^{-6}$ to $3\times10^{-3}$.

10. The method claim 9, wherein the peptide selected has an apparent dissociation constant, $k_d$, with a value of approximately $1\times10^{-2}$ to $1\times10^{-1}$.

11. The method of any one of claims 1–10, wherein the immobilized nucleic acid molecule is a plasmid.

12. A method of transfecting cells with nucleic acid comprising the step of providing a nucleic acid condensing peptide/condensed nucleic acid complex, wherein a peptide of said complex has an equilibrium rate constant, $K_D$, with a value of approximately $1\times10^{-12}$ to $1\times10^{31\ 6}$.

13. A method of transfecting cells with nucleic acid comprising the step of providing a nucleic acid peptide/condensed nucleic acid complex, wherein a peptide of said complex has an apparent dissociation constant, $k_d$, with a value of approximately $1\times10^{-6}$ to $3\times10^{-3}$.

14. The method of claim 13, wherein said apparent dissociation constant, $k_d$, has a value of approximately $1\times10^{-2}$ to $1\times10^{-1}$.

15. A method of transfecting cells with nucleic acid comprising delivering to the cell a nucleic acid condensing peptide/nucleic acid complex wherein a peptide of said complex has an apparent dissociation constant, $k_d$, with a value of approximately $1\times10^{-6}$ to $3\times10^{-3}$.

16. The method of claim 15 wherein said apparent dissociation constant, $k_d$, is approximately $1\times10^{-2}$ to $3\times10^{-1}$.

17. A method of measuring the equilibrium rate constant, $K_D$ (or apparent dissociation constant, $k_d$) for a peptide binding to plasmid nucleic acid comprising:

immobilizing the plasmid nucleic acid on a sensor chip;

exposing the immobilized nucleic acid molecule to a solution of a test peptide;

detecting and recording a change in the surface plasmon resonance upon binding of the peptide to the immobilized nucleic acid; and calculating the equilibrium constant $K_D$ (or apparent dissociation constant, $k_d$) of the test peptide from the recorded change in surface plasmon resonance.

18. In a method of delivering a recombinant nucleic acid to a population of host cells, the improvement comprising obtaining optimal transfection of said cells comprising determining the equilibrium constant $K_D$ of a peptide that is present in a complex comprising a nucleic acid condensing peptide and a condensed nucleic acid for transfection from a change in surface plasmon resonance which occurs upon binding of the peptide to and dissociation of the peptide from an immobilized nucleic acid.

19. In a method of delivering a recombinant nucleic acid to a population of host dells, the improvement comprising obtaining optimal transfection of said cells comprising determining the apparent dissociation constant, $k_d$ of a peptide that is present in a complex comprising a nucleic acid condensing peptide and a condensed nucleic acid for transfection from a change in surface plasmon resonance which occurs upon dissociation of the peptide from an immobilized nucleic acid.

20. The method of claim 18 or 19, further comprising the steps of selecting an equilibrium rate constant, $K_D$, with a value of approximately $1\times10^{-9}$ to $1\times10^{-6}$ or apparent dissociation constant, $k_d$, with a value of approximately $1\times10^{-4}$ to $3\times10^{-3}$.

* * * * *

UNITED STATES PATENT AND TRADEMARK OFFICE
CERTIFICATE OF CORRECTION

PATENT NO. : 6,218,112 B1
DATED : April 17, 2001
INVENTOR(S) : Thatcher et al.

It is certified that error appears in the above-identified patent and that said Letters Patent is hereby corrected as shown below:

Title page,
Item [56], FOREIGN PATENT DOCUMENTS, please insert the following:

-- WO 91/17773      11/28/91      (PCT) --

OTHER PUBLICATIONS, please insert the following: --

Cheskis, B. et al., "Modulation of Nuclear Receptor Interactions by Ligands: Kinetic Analysis Using Surface Plasmon Resonance", Biochem., 1996, 35, 3309-3318

Fisher, R. J. et al., "Surface plasmon resonance based methods for measuring the kinetics and binding affinities of biomolecular interactions", Curr. Opin. Biotech., 1994, 5, 389-395;

Parsons, I.D. et al., "Probing the molecular mechanism of action of co-repressor in the E. coli methionine repressor-operator complex using surface plasmon resonance (SPR)", Nucl. Acids Res., 1995, 23 (2), 211-216;

Saijo, M. et al., "Sequential binding of DNA repair proteins RPA and ERCC1 tp XPA in vitro", Nucl. Acis Res., 1996, 24 (23), 4170-4724;

Wagner, E. et al., "Influenza virus hemagglutinin HA-2-N-terminal fusogenic peptides augment gene transfer by transferin - polylysine - DNA complexes: Toward a synthetic virus-like gene-transfer vehicle", Proc. Natl. Acad. Sci. USA, 1992, 89, 7934-7938;

Cotton and Wagner, 1993, Current Opinion in Biotechnology 4: 705-710;

Fisher et al., 1994, Protein Science 3:257-266;

Löfas and Johnsson, 1990, J. Chem. Soc., Chem. Commun: 1526-1528;

Zabner, et al., 1995, J. Biol. Chem., 270: 18997-19007;

Chiang et al., 1992, Proc. Natl. Acad. Sci USA 89: 5799-5803 --;

UNITED STATES PATENT AND TRADEMARK OFFICE
CERTIFICATE OF CORRECTION

PATENT NO. : 6,218,112 B1
DATED : April 17, 2001
INVENTOR(S) : Thatcher et al.

It is certified that error appears in the above-identified patent and that said Letters Patent is hereby corrected as shown below:

Column 9,
Line 56, please delete "homolpeptide" and insert therefor -- homopeptide --;

Column 16,
Line 26, please delete "KKAKAVKPK-AAKPKKPKKKRKVEKKS" and insert therefor -- KAKAKAVKPK-AAKPKKPKKKRKVEKKS --;
Line 27, please delete "KKAKKPAAC (Acm)-COOH (SEQ ID NO: 7)" and insert therefor -- PKKAKKPAAC (ACM)-COOH (SEQ ID NO: 7) --;
Line 38, please delete "NBC7 NH2-TRPAWRRAKRRAARRCGVSARRA" and insert therefor -- NBC7 NH2-TRRAWRRAKRRAARRCGVSARRA --;

Column 50,
Line 2, please delete "$1x12^{-12}$" and insert therefor -- $-1x10^{-12}$ --;

Column 51,
Line 33, please delete "$1x10^{31\ 6}$" and insert therefor -- $1x10^6$ --;

Signed and Sealed this

Thirteenth Day of May, 2003

JAMES E. ROGAN
*Director of the United States Patent and Trademark Office*

SEQUENCE LISTING

<160> NUMBER OF SEQ ID NOS: 25

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Peptide

<400> SEQUENCE: 1

Thr Arg Arg Ala Trp Arg Arg Ala Lys Arg Ala Ala Arg Arg Cys
 1               5                  10                  15

Gly Val Ser Ala Arg Arg Ala Ala Arg Arg Ala Trp Arg Arg Glu
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Peptide

<400> SEQUENCE: 2

Thr Lys Lys Ala Trp Lys Lys Ala Glu Lys Lys Ala Ala Lys Lys Cys
 1               5                  10                  15

Gly Val Ser Ala Lys Lys Ala Ala Lys Lys Ala Trp Lys Lys Ala
            20                  25                  30

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: UNSURE
<222> LOCATION: (3)
<223> OTHER INFORMATION: Xaa is Ser or Thr or Pro
<220> FEATURE:
<221> NAME/KEY: UNSURE
<222> LOCATION: (7)
<223> OTHER INFORMATION: Xaa is Ala or Pro or Val
<220> FEATURE:
<221> NAME/KEY: UNSURE
<222> LOCATION: (8)
<223> OTHER INFORMATION: Xaa is Ala or Thr or Lys or Pro
<220> FEATURE:
<221> NAME/KEY: UNSURE
<222> LOCATION: (9)
<223> OTHER INFORMATION: Xaa is Lys or Ala or Thr or Val
<220> FEATURE:
<221> NAME/KEY: UNSURE
<222> LOCATION: (12)
<223> OTHER INFORMATION: Xaa is Ala or Val

<400> SEQUENCE: 3

Lys Lys Xaa Pro Lys Lys Xaa Xaa Xaa Pro Ala Xaa
 1               5                  10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: UNSURE
<222> LOCATION: (1)

```
<223> OTHER INFORMATION: Xaa is Ala or Val

<400> SEQUENCE: 4

Xaa Lys Ser Pro Ala Lys Ala Lys Ala
 1               5

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: UNSURE
<222> LOCATION: (1)
<223> OTHER INFORMATION: Xaa is Lys or Arg
<220> FEATURE:
<221> NAME/KEY: UNSURE
<222> LOCATION: (2)
<223> OTHER INFORMATION: Xaa is Ala or Val or Thr
<220> FEATURE:
<221> NAME/KEY: UNSURE
<222> LOCATION: (10)
<223> OTHER INFORMATION: Xaa is Pro or Ala or Ser
<220> FEATURE:
<221> NAME/KEY: UNSURE
<222> LOCATION: (12)
<223> OTHER INFORMATION: Xaa is Ala or Lys or Thr or Val

<400> SEQUENCE: 5

Xaa Xaa Val Lys Pro Lys Ala Ala Lys Xaa Lys Xaa
 1               5                  10

<210> SEQ ID NO 6
<211> LENGTH: 61
<212> TYPE: PRT
<213> ORGANISM: Artificial Sequence
<220> FEATURE:
<223> OTHER INFORMATION: Description of Artificial Sequence: Peptide

<400> SEQUENCE: 6

Pro Lys Lys Lys Arg Lys Val Glu Lys Lys Ser Pro Lys Ala Lys
 1               5                  10                  15

Lys Pro Ala Ala Lys Ser Pro Ala Lys Ala Lys Ala Val Lys
            20                  25                  30

Pro Lys Ala Ala Lys Pro Lys Lys Pro Lys Lys Arg Lys Val Glu
            35                  40                  45

Lys Lys Ser Pro Lys Lys Ala Lys Pro Ala Ala Cys
            50                  55                  60

<210> SEQ ID NO 7
<211> LENGTH: 61
<212> TYPE: PRT
<213> ORGANISM: Artificial Sequence
<220> FEATURE:
<223> OTHER INFORMATION: Description of Artificial Sequence: Peptide

<400> SEQUENCE: 7

Pro Lys Lys Lys Arg Lys Val Glu Lys Lys Ser Pro Lys Ala Lys
 1               5                  10                  15

Lys Pro Ala Ala Lys Ser Pro Ala Lys Ala Lys Ala Val Lys
            20                  25                  30

Pro Lys Ala Ala Lys Pro Lys Lys Pro Lys Lys Arg Lys Val Glu
            35                  40                  45

Lys Lys Ser Pro Lys Lys Ala Lys Pro Ala Ala Cys
            50                  55                  60
```

```
<210> SEQ ID NO 8
<211> LENGTH:
<212> TYPE:
<213> ORGANISM:

<400> SEQUENCE: 8

This Sequence is intentionally skipped

<210> SEQ ID NO 9
<211> LENGTH:
<212> TYPE:
<213> ORGANISM:

<400> SEQUENCE: 9

This Sequence is intentionally skipped

<210> SEQ ID NO 10
<211> LENGTH:
<212> TYPE:
<213> ORGANISM:

<400> SEQUENCE: 10

This Sequence is intentionally skipped

<210> SEQ ID NO 11
<211> LENGTH: 30
<212> TYPE: PRT
<213> ORGANISM: Artificial Sequence
<220> FEATURE:
<221> NAME/KEY: UNSURE
<222> LOCATION: (30)
<223> OTHER INFORMATION: Xaa is Cys with Acm sidechain
<220> FEATURE:
<223> OTHER INFORMATION: Description of Artificial Sequence: Peptide

<400> SEQUENCE: 11

Lys Pro Lys Ala Ala Lys Pro Lys Pro Lys Lys Lys Arg Lys Val
 1               5                  10                  15

Glu Lys Lys Ser Pro Lys Lys Ala Lys Lys Pro Ala Ala Xaa
            20                  25                  30

<210> SEQ ID NO 12
<211> LENGTH: 25
<212> TYPE: PRT
<213> ORGANISM: Artificial Sequence
<220> FEATURE:
<221> NAME/KEY: UNSURE
<222> LOCATION: (25)
<223> OTHER INFORMATION: Xaa is Cys with Acm sidechain
<220> FEATURE:
<223> OTHER INFORMATION: Description of Artificial Sequence: Peptide

<400> SEQUENCE: 12

Lys Lys Ser Pro Lys Lys Ala Lys Lys Pro Ala Ala Lys Lys Ser Pro
 1               5                  10                  15

Lys Lys Ala Lys Lys Pro Ala Tyr Xaa
            20                  25

<210> SEQ ID NO 13
<211> LENGTH: 37
<212> TYPE: PRT
<213> ORGANISM: Artificial Sequence
<220> FEATURE:
<221> NAME/KEY: UNSURE
<222> LOCATION: (37)
```

```
<223> OTHER INFORMATION: Xaa is Cys with Acm sidechain
<220> FEATURE:
<223> OTHER INFORMATION: Description of Artificial Sequence: Peptide

<400> SEQUENCE: 13

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
            20                  25                  30

Lys Pro Ala Tyr Xaa
        35

<210> SEQ ID NO 14
<211> LENGTH: 49
<212> TYPE: PRT
<213> ORGANISM: Artificial Sequence
<220> FEATURE:
<221> NAME/KEY: UNSURE
<222> LOCATION: (49)
<223> OTHER INFORMATION: Xaa is Cys with Acm sidechain
<220> FEATURE:
<223> OTHER INFORMATION: Description of Artificial Sequence: Peptide

<400> SEQUENCE: 14

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
            20                  25                  30

Lys Pro Ala Ala Lys Lys Ser Pro Lys Lys Ala Lys Lys Pro Ala Tyr
            35                  40                  45

Xaa

<210> SEQ ID NO 15
<211> LENGTH: 11
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa  is preferably Lysine or Threonine
<220> FEATURE:
<221> NAME/KEY: UNSURE
<222> LOCATION: (2)
<223> OTHER INFORMATION: Xaa  is preferably Glycine or Glutamine
<220> FEATURE:
<221> NAME/KEY: UNSURE
<222> LOCATION: (3)
<223> OTHER INFORMATION: Xaa  is preferably Glycine, but can also be
      Asparatate, Glutamate, or Serine
<220> FEATURE:
<221> NAME/KEY: UNSURE
<222> LOCATION: (4)
<223> OTHER INFORMATION: Xaa  is preferably Glycine,  but can also be
      Lysine, Valine, Glutamine, or Threonine
<220> FEATURE:
<221> NAME/KEY: UNSURE
<222> LOCATION: (5)
<223> OTHER INFORMATION: Xaa is preferably Lysine or Alanine
<220> FEATURE:
<221> NAME/KEY: UNSURE
<222> LOCATION: (6)
<223> OTHER INFORMATION: Xaa  is preferably Alanine or Lysine
<220> FEATURE:
<221> NAME/KEY: UNSURE
<222> LOCATION: (7)
<223> OTHER INFORMATION: Xaa is preferably Arginine, but can also be Valine
      or Isoleucine.
<220> FEATURE:
<221> NAME/KEY: UNSURE
<222> LOCATION: (8)
```

```
<223> OTHER INFORMATION: Xaa is preferably Alanine, but can also be
      Threonine, Histidine, or Proline
<220> FEATURE:
<221> NAME/KEY: UNSURE
<222> LOCATION: (9)
<223> OTHER INFORMATION: Xaa is preferably Lysine, Arginine, or Glutamine
<220> FEATURE:
<221> NAME/KEY: UNSURE
<222> LOCATION: (10)
<223> OTHER INFORMATION: Xaa is Alanine or Arginine
<220> FEATURE:
<221> NAME/KEY: UNSURE
<222> LOCATION: (11)
<223> OTHER INFORMATION: Xaa is preferably Lysine or Glutamine
<220> FEATURE:
<223> OTHER INFORMATION: Description of Artificial Sequence: Peptide

<400> SEQUENCE: 15

Xaa Xaa Xaa Xaa Xaa Xaa Xaa Xaa Xaa Xaa Xaa
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Peptide

<400> SEQUENCE: 16

Lys Gly Gly Gly Lys Ala Arg Ala Lys Ala Lys
 1               5                  10

<210> SEQ ID NO 17
<211> LENGTH:
<212> TYPE:
<213> ORGANISM:

<400> SEQUENCE: 17

This Sequence is intentionally skipped

<210> SEQ ID NO 18
<211> LENGTH: 35
<212> TYPE: PRT
<213> ORGANISM: Artificial Sequence
<220> FEATURE:
<221> NAME/KEY: UNSURE
<222> LOCATION: (35)
<223> OTHER INFORMATION: Xaa is Cys with Acm sidechain
<220> FEATURE:
<223> OTHER INFORMATION: Description of Artificial Sequence: Peptide

<400> SEQUENCE: 18

Lys Lys Ala Lys Ser Pro Ala Lys Ala Lys Ala Lys Ala Val Lys Pro
 1               5                  10                  15

Lys Ala Ala Lys Pro Lys Lys Ser Pro Lys Lys Ala Lys Lys Pro Ala
                20                  25                  30

Tyr Ala Xaa
        35

<210> SEQ ID NO 19
<211> LENGTH: 30
<212> TYPE: PRT
<213> ORGANISM: Artificial Sequence
<220> FEATURE:
<221> NAME/KEY: UNSURE
<222> LOCATION: (30)
<223> OTHER INFORMATION: Xaa is Cys with Acm sidechain
<220> FEATURE:
<223> OTHER INFORMATION: Description of Artificial Sequence: Peptide
```

-continued

<400> SEQUENCE: 19

Lys Pro Lys Ala Ala Lys Pro Lys Lys Glu Val Lys Arg Lys Lys Lys
1               5                   10                  15

Pro Lys Lys Ser Pro Lys Lys Ala Lys Lys Pro Ala Ala Xaa
            20                  25                  30

<210> SEQ ID NO 20
<211> LENGTH: 37
<212> TYPE: PRT
<213> ORGANISM: Artificial Sequence
<220> FEATURE:
<221> NAME/KEY: UNSURE
<222> LOCATION: (37)
<223> OTHER INFORMATION: Xaa is Cys with Acm sidechain
<220> FEATURE:
<223> OTHER INFORMATION: Description of Artificial Sequence: Peptide

<400> SEQUENCE: 20

Lys Ala Lys Ala Lys Ala Lys Pro Lys Ala Lys Ala Lys Ala Lys Pro
1               5                   10                  15

Lys Ala Lys Ala Lys Ala Lys Pro Lys Ala Lys Ala Lys Ala Lys Pro
            20                  25                  30

Lys Ala Lys Ala Xaa
            35

<210> SEQ ID NO 21
<211> LENGTH: 38
<212> TYPE: PRT
<213> ORGANISM: Artificial Sequence
<220> FEATURE:
<221> NAME/KEY: UNSURE
<222> LOCATION: (38)
<223> OTHER INFORMATION: Xaa is Cys with Acm sidechain
<220> FEATURE:
<223> OTHER INFORMATION: Description of Artificial Sequence: Peptide

<400> SEQUENCE: 21

Thr Lys Lys Ser Pro Lys Lys Ala Lys Lys Pro Ala Ala Lys Lys Ser
1               5                   10                  15

Pro Lys Lys Ala Lys Lys Pro Ala Ala Lys Lys Ser Pro Lys Lys Ala
            20                  25                  30

Lys Lys Pro Ala Ala Xaa
            35

<210> SEQ ID NO 22
<211> LENGTH: 38
<212> TYPE: PRT
<213> ORGANISM: Artificial Sequence
<220> FEATURE:
<221> NAME/KEY: UNSURE
<222> LOCATION: (38)
<223> OTHER INFORMATION: Xaa is Cys with Acm sidechain
<220> FEATURE:
<223> OTHER INFORMATION: Description of Artificial Sequence: Peptide

<400> SEQUENCE: 22

Thr Lys Lys Ser Pro Lys Lys Ala Lys Lys Pro Ala Ala Lys Lys Ser
1               5                   10                  15

Pro Lys Lys Ala Lys Lys Pro Ala Ala Lys Lys Ser Pro Lys Lys Ala
            20                  25                  30

Lys Lys Pro Ala Tyr Xaa
            35

-continued

```
<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Peptide

<400> SEQUENCE: 23

Thr Lys Lys Lys Lys Lys Lys Lys Lys Lys Lys Lys Lys Lys Lys
 1               5                  10                  15

Lys Lys Lys Cys
            20

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Peptide

<400> SEQUENCE: 24

Lys Lys Lys Gly Gly Tyr Cys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Peptide

<400> SEQUENCE: 25

Pro Lys Lys Lys Arg Lys Val Glu
 1               5
```